(12) United States Patent
Qvist et al.

(10) Patent No.: US 6,355,442 B1
(45) Date of Patent: Mar. 12, 2002

(54) METHOD OF ASSAYING COLLAGEN FRAGMENTS IN BODY FLUIDS, A TEST KIT AND MEANS FOR CARRYING OUT THE METHOD AND USE OF THE METHOD TO DIAGNOSE THE PRESENCE OF DISORDERS ASSOCIATED WITH THE METABOLISM OF COLLAGEN

(75) Inventors: Per Qvist, Klampenborg; Martin Bonde, Lyngby, both of (DK)

(73) Assignee: Osteometer Biotech A/S, Herlev (DK)

( * ) Notice: Subject to any disclaimer, the term of this patent is extended or adjusted under 35 U.S.C. 154(b) by 0 days.

(21) Appl. No.: 09/548,608

(22) Filed: Apr. 13, 2000

Related U.S. Application Data

(62) Division of application No. 08/963,825, filed on Nov. 4, 1997, now Pat. No. 6,110,689, which is a continuation of application No. 08/187,319, filed on Jan. 21, 1994, now abandoned.

(51) Int. Cl.[7] .............................................. G01N 33/53
(52) U.S. Cl. ...................... 435/7.1; 435/7.93; 436/518; 436/531; 530/328; 530/356; 530/387.9; 530/388.1
(58) Field of Search ................................ 530/328, 356, 530/387.9, 388.1; 435/7.1, 7.93; 436/518, 531

(56) References Cited

U.S. PATENT DOCUMENTS

| | | | | |
|---|---|---|---|---|
| 4,134,792 A | * | 1/1979 | Boguslaski et al. | 195/99 |
| 4,628,027 A | | 12/1986 | Gay | |
| 5,300,434 A | * | 4/1994 | Eyre | 435/548 |
| 5,320,970 A | | 6/1994 | Eyre | |
| 5,455,179 A | | 10/1995 | Eyre | |
| 5,472,884 A | | 12/1995 | Eyre | |
| 5,473,052 A | | 12/1995 | Eyre | |
| 5,532,169 A | | 7/1996 | Eyre | |
| 5,576,189 A | | 11/1996 | Eyre | |
| 5,607,862 A | | 3/1997 | Eyre | |
| 5,750,647 A | * | 5/1998 | Eyre et al. | 530/328 |
| 5,962,639 A | * | 10/1999 | Eyre | 530/329 |

FOREIGN PATENT DOCUMENTS

| | | |
|---|---|---|
| EP | 0 394 296 B1 | 10/1990 |
| EP | 0 424 428 B1 | 5/1991 |
| EP | 0 502 928 B1 | 9/1992 |
| WO | WO 83/04104 | 11/1983 |
| WO | WO 88 08980 | 11/1988 |
| WO | WO 90 04417 | 5/1990 |
| WO | WO 92/21698 | 12/1992 |
| WO | WO 94/14844 | 7/1994 |
| WO | WO 95/04282 | 2/1995 |

OTHER PUBLICATIONS

Beardsworth et al., 1990, "Changes with age in the urinary excretion of lysyl– and hydroxylysylpyridinoline, two new markers of bone collagen turnover", *J. Bone Miner. Res.* 5:671–676.

Black et al., 1988, "Quantitative analysis of the pyridinium crosslinks of collagen in urine using ion–paired reversed–phase high–performance liquid chromatography", *Ana. Biochem.* 169:197–203.

del Pozo et al., 1986, "Binding of 1–anilinoaphthalene–8–sulfonic acid to type I collagen" *Int. J. Pept. Protein Res.* 28:173–178.

P.D. Delmas, 1990, "Biochemical markers of bone turnover for the clinical assessment of metabolic bone disease", *Metabolic Bone Dis.* 19:1–18.

Dickson et al., 1993, "Pyridonolines and cross–linked type I collagen N–telopeptides as markers of bone metastases in breast cancer", 15th Annual Mtg of the Amer. Soc. for Bone & Min. Res., Tampa, Fl., Sep., 8:S288, Abstr. 686.

Eyre et al., 1988, "Identification of urinary peptides derived from cross–linking sites in bone collagen in Paget's disease", *J. of Bone & Mineral Res* 3:S210, Abstr.565.

D.R. Eyre, 1994, "New molecular markers of bone metabolism", Ther. Res. (Symposium) 15:532–535.

D. Fujimoto, 1980, "Evidence for natural existence of pyridinoline crosslink in collagen", *Biochem. & Biophys. Res. Comm.* 93:948–953.

Fujimoto et al., 1983, "Analysis of pyridinoline, a cross–linking compound of collagen fibers, in human urine", *J. Biochem.* 94:1133–1136.

H. Furthmayr, 1982, "Immunization procedures, isolation by affinity chromatography, and serological and immunochemical characterization of collagen specific antibodies", *Immunochemistry of the extracellular matrix*, H. Furthmayr (ed.), CRC Press, vol. 1, Chap. 11, pp. 143–178.

(List continued on next page.)

*Primary Examiner*—Jeffrey Stucker
(74) *Attorney, Agent, or Firm*—Pennie & Edmonds LLP

(57) ABSTRACT

A method of assaying collagen fragments in body fluids, including bringing a sample of body fluid in contact with at least one immunological binding partner for the collagen fragments, said binding partner being immunoreactive with synthetic peptides, the sequences of which are essentially derived from collagen and containing potential sites for cross-linking. The immunological binding partners are incorporated, either as whole antibodies or as immunologically active fragments thereof, in an assay for quantitative determination of collagen fragments in the sample. In addition to being contacted with the immunological binding partner(s), the sample may be brought into direct contact with the corresponding synthetic peptide. The invention further comprises a test kit and specific means for carrying out the method. The structure of specific peptides is also described.

11 Claims, 7 Drawing Sheets

OTHER PUBLICATIONS

Gertz et al., 1994, "Monitoring bone resorption in early postmenopausal women by an immunoassay for cross–linked collagen peptides in urine", *J. of Bone & Min. Res.* 9:135–142.

Gunja–Smith & Boucek, 1981 "Collagen cross–linking compounds in human urine", *Biochem. J.* 197:759–782.

Hanson et al., 1992, "A specific immunoassay for monitoring human bone resorption: Quantitation of type I collagen cross–linked N–telopeptides in urine", *J. of Bone & Min. Res.* 7:1251–1258.

Hassager et al., 1994, "The carboxy–terminal pyridinoline cross–linked telopeptide of type I collagen in serum as a marker of bone resorption: The effect of nandrolone decanoate and hormone replacement therapy", *Calcif. Tissue Int.* 54:30–33.

Henkel et al., 1987, "Characterization of a type–I collagen trimeric cross–linked peptide from calf aorta and it cross–linked structure", *Eur. J. Biochem.* 165:427–436.

Kruger–Franke, 1991, "Pyridinoline–containing collagen degradation products in the urine of patients with osteoarthrosis of the hip joint", *Z. Rheumatol.* 50:323–327 (German with English Translation).

Kuboki et al., 1981, "Location of the intermolecular cross–links in bovine dentin collagen, solubilization with trypsin and isolation of cross–link peptides containing dihydroxylysinonorleucine and pyridinoline", *Biochem. & Biophys. Res. Comm.* 102:119–126.

K. Kuhn, 1982, "Chemical properties of collagen", *Immunochemistry of the Extracellular Matrix*, H. Furthmayr (ed.), CRC Press, vol. 1, Chap. 1, pp. 1–23.

K. Kuhn, 1987, "The classical collagens: Types I, II, and III", *Structure & Function of Collagen Types*, Mayne & Bergeson (eds.), Academic Press, Chap. 1, pp. 10–23.

Kuypers et al., 1992, "Identification of the loci of the collagen–associated Ehrlich chromogen in type I collagen confirms its role as a trivalent cross–link", *Biochem. J.* 283:129–136.

Macek & Adam, 1987, "Determination of collagen degradation products in human urine in osteoarthrosis", *Z. Rheumatol.* 46:237–240.

Otter et al., 1988, "Type I collagen α–1 chain c–telopeptide: Solution structure determined by 600–MHZ proton NMR spectroscopy and implications for its role in collagen fibrillogenesis", *Biochem.* 27:3560–3567.

Rennard et al., 1980, "Enzyme–linked immunoassay (ELISA) for connective tissue components", *Anal. Biochem.* 104:205–214.

Risteli & Risteli, 1986, "Radioimmunoassay for monitoring connective tissue metabolism", *Rheumatol.* 10:216–245.

Risteli et al., 1993, "Radioimmunoassay for the pyridinoline cross–linked carboxy–terminal telopeptide of type I collagen: A new serum marker of bone collagen degradation", *Clin. Chem.* 39:635–640.

S.P. Robins, 1982, "An enzyme–linked immunoassay for the collagen cross–link pyridinoline", *Biochem. J.* 207:617–620.

Robins et al., 1987, "Measurement of hydroxypyridinium crosslinks of collagen as an index of bone matrix degradation", Paper, Lake Garda, Italy, p. 23, Abstr. OP45.

Rodriguiz et al., 1993, "Type I Collagen cross–linked N–telopeptide by osteopetrotic patients during interferon gamma therapy: A correlation with bone biochemical and densitometric markers", $15^{th}$ Annual Mtg of the Amer. Soc. for Bone & Min. Res., Tampa, Fl., Sep., 8:S291, Abstr. 698.

Rohde et al., 1983, "Serum and urine analysis of the aminoterminal procollagen peptide type III by radioimmunoassay with antibody fab fragments", *Collagen Rel. Res.* 3:371–379.

Schuppan et al., 1986, "Radioimmunoassay for the carboxy––terminal cross–linking domain of type IV (basement membrane) procollagen in body fluids", *J. Clin. Invest.* 78:241–248.

P.G. Scott, 1986, "Spectropic study of environment–dependent changes in the confirmation of the isolated carboxy–terminal telopeptide of type I collagen", *Biochem.* 25:974–980

Tellerova et al., 1986, "Determination of larger urinary peptides in osteoarthrosis by high–performance liquid chromatography", *Scand. J. Rheumatol.* 15:52–56.

Eyre et al., 1984, "Quantitation of Hydroxypyridinium Crosslinks in Collagen by High–Performance Liquid Chromatography", *Analytical Biochemistry* 137:380.

\* cited by examiner

METHOD OF ASSAYING COLLAGEN FRAGMENTS IN BODY FLUIDS, A TEST KIT AND MEANS FOR CARRYING OUT THE METHOD AND USE OF THE METHOD TO DIAGNOSE THE PRESENCE OF DISORDERS ASSOCIATED WITH THE METABOLISM OF COLLAGEN

This is a division of application Ser. No. 08/963,825, filed Nov. 4, 1997, now U.S. Pat. No. 6,110,689, which is a continuation of Ser. No. 08/187,319, filed Jan. 24, 1994, now abandoned.

The present invention relates to a method of determining collagen fragments in body fluids. The invention further relates to means, including synthetic peptides, monoclonal and polyclonal antibodies and cell lines, for use in carrying out the method of the invention. Still further, the invention relates to the use of the above method to diagnose the presence of disorders associated with the metabolism of collagen, especially osteoporosis.

BACKGROUND OF THE INVENTION

Collagens and Disorders of Collagen Metabolism

Osteoporosis is the most common bone disease in humans. Primary osteoporosis, accompanied by increased susceptibility to fractures, results from a progressive reduction in skeletal bone mass. It is estimated to affect 15–20 million individuals in the USA alone. Its basis is an age-dependent imbalance in bone remodeling, i.e., in the rates of formation and resorption of bone tissue.

In the USA about 1.2 million osteoporosis-related fractures occur in the elderly each year including about 538,000 compression fractures of the spine, about 227,000 hip fractures and a substantial number of early fractured peripheral bones. Between 12 and 20% of the hip fractures are fatal because they cause severe trauma and bleeding, and half of the surviving patients require nursing home care. Total costs from osteoporosis-related injuries now amount to at least $10 billion annually in the USA (Riggs, *New England Journal of Medicine* 327:620–627 (1992)).

Osteoporosis is most common in postmenopausal women who, on average, lose 15% of their bone mass in the 10 years after menopause. This disease also occurs in men as they get older and in young amenorrheic women athletes. Despite the major, and growing, social and economic consequences of osteoporosis, the availability of reliable assays for measuring bone resorption rates in patients or in healthy subjects is very limited. Other disorders entailing (and correlated with) abnormalities in collagen metabolism include Paget's disease, Marfan's syndrome, osteogenesis imperfecta neoplastic growth in collagenous tissue, dwarfism, rheumatoid arthritis, osteoarthritis and vasculitis syndrome.

Three known classes of human collagen have been described to date. The Class I collagens, subdivided into types I, II, III, V, and XI, are known to form fibrils. Their full amino-acid sequence (to the extent they have been elucidated) are attached in Appendix A.

Collagen type I accounts for more than 90% of the organic matrix of bone. Therefore, in principle, it is possible to estimate the rate of bone resorption by monitoring the degradation of collagen type I. Likewise, a number of other disease states involving connective tissue can be monitored by determining the degradation of collagen. Examples are collagen type II degradation associated with rheumatoid arthritis and osteoarthritis and collagen type III degradation in vasculitis syndrome.

Amino acid sequences of human type III collagen, human pro 1(II) collagen, and the entire prepro 1(III) chain of human type III collagen and corresponding cDNA clones have been investigated and determined by several groups of researchers; see Loil et al., *Nucleic Acids Research* 12:9383–9394 (1984); Sangiorgi et al., *Nucleic Acids Research* 13:2207–2225 (1985); Baldwin et al., *Biochem J.* 262:521–528 (1989); and Ala-Kokko et al., *Biochem. J.* 260:509–516 (1989).

Type I, II, and III collagens are all formed in the organism as procollagen molecules, comprising N-terminal and C-terminal propeptide sequences, which are attached to the core collagen molecules. After removal of the propeptides, which occur naturally in vivo during collagen synthesis, the remaining core of the collagen molecules consists largely of a triple-helical domain having terminal telopeptide sequences which are non-triple-helical. These telopeptide sequences have an important function as sites of intermolecular cross-linking of collagen fibrils extracellularly. The alpha-helical region also includes crosslinkable sites. Peptides from this region are part of the present invention.

Intermolecular cross-links provide collagen fibrils with biomechanical stability. The formation of these cross-links is initiated by modification of lysine and hydroxylysine residues to the corresponding aldehydes. Several of these residues located on adjacent chains of collagen will spontaneously form different intermolecular cross-links. The exact position of the sites for cross-linking on collagen telopeptides and from the helical region has been previously described. See, for example, Kühn, K., in *Immunochemistry of the Extracellular Matrix* 1:1–29, CRC Press, Inc., Boca Raton, Fla. (1982), Eyre, D. R., *Ann. Rev. Biochem.* 53:717–48 (1984) or U.S. Pat. No. 5,140,103). Furthermore, the amino acid sequences of some potential sites for cross-linking in type I, II, and III collagen are given in Table 1 below.

The fibrous proteins, collagen and elastin, are cross-linked by a unique mechanism based on aldehyde formation from lysine or hydroxylysine side chains. Four homologous loci of cross-linking are evident in molecules of type I, II and III collagens (for review see Kühn, K., in *Immunochemistry of the Extracellular Matrix* 1:1–29 (1982)). Two are aldehyde sites, one in each telopeptide region. The other two sites are hydroxylysine symmetrically placed at about 90 residues from each end of the molecule. When collagen molecules pack into fibrils, these latter sites in the helical region align and react with telopeptide aldehydes in adjacent molecules. There is now strong evidence that 3-hydroxypyridinium residues are the mature cross-link coming from hydroxylysine-derived aldehydes. The mature cross-linking residues of the other pathway, i.e. from aldehyde formation of lysine residues, is, however, still unknown.

Prior Art Assays for Collagen Degradation

In the past, assays have been developed for monitoring degradation of collagen in vivo by measuring various biochemical markers, some of which have been degradation products of collagen. However, none of these methods are based upon the use of immunological binding partners in the form of antibodies which are immunoreactive with synthetic peptides having a sequence essentially derived from collagen fragments having crosslinkable sites.

For example, hydroxyproline, an amino acid largely restricted to collagen, and the principal structural protein in bone and all other connective tissues, is excreted in urine. Its excretion rate is known to be increased in certain conditions, notably Paget's disease, a metabolic bone disorder in which bone turnover is greatly increased, as discussed further below.

For this reason, urinary hydroxyproline has been used extensively as an amino acid marker for collagen degradation; Singer, F. R. et al., *Metabolic Bone Disease*, Vol. II (eds. Avioli, L. V., and Kane, S. M.), 489–575 (1978), Academic Press, New York.

U.S. Pat. No. 3,600,132 discloses a process for the determination of hydroxyproline in body fluids such as serum, urine, lumbar fluid and other intercellular fluids in order to monitor deviations in collagen metabolism. The patent states that hydroxyproline correlates with increased collagen anabolism or catabolism associated with pathological conditions such as Paget's disease, Marfan's syndrome, osteogenesis imperfecta, neoplastic growth in collagen tissues and in various forms of dwarfism.

Bone resorption associated with Paget's disease has also been monitored by measuring small peptides containing hydroxyproline, which are excreted in the urine following degradation of bone collagen; Russell et al., *Metab. Bone Dis. and Rel. Res.* 4 and 5:255–262 (1981), and Singer, F. R., et al., supra.

In the case of Paget's disease, the increased urinary hydroxyproline probably comes largely from bone degradation; hydroxyproline, however, generally cannot be used as a specific index for bone degradation. Much of the hydroxyproline in urine may come from new collagen synthesis (considerable amounts of the newly made protein are degraded and excreted without ever becoming incorporated into tissue fabric), and from turnover of certain blood proteins as well as other proteins that contain hydroxyproline.

Furthermore, about 80% of the free hydroxyproline derived from protein degradation is metabolized in the liver and never appears in the urine. Kiviriko, K. I., *Int. Rev. Connect. Tissue Res.* 5:93 (1970), and Weiss, P. H. and Klein, L., *J. Clin. Invest.* 48:1 (1969). Hydroxyproline is a good marker for osteoporosis, but it is troublesome to handle. It is specific for collagen in bones.

Hydroxylysine and its glycoside derivatives, both peculiar to collagenous proteins, have been considered to be more accurate than hydroxyproline as markers of collagen degradation. However, for the same reasons described above for hydroxyproline, hydroxylysine and its glycosides are probably equally non-specific markers of bone resorption; Krane, S. M. and Simon, L. S., *Develop. Biochem.* 22:185 (1981).

Other researchers have measured the cross-linking compound 3-hydroxypyridinium in urine as an index of collagen degradation in joint diseases. See, for background and as examples, Wu and Eyre, *Biochemistry* 23:1850 (1984); Black et al., *Annals of the Rheumatic Diseases* 48:641–644 (1989); Robins et al.; *Annals of the Rheumatic Diseases* 45:969–973 (1986); and Seibel et al., *The Journal of Dermatology* 16:964 (1989). In contrast to the present invention, these prior researchers have hydrolyzed peptides from body fluids and then looked for the presence of individual 3-hydroxypyridinium residues.

Assays for determination of the degradation of type I, II, and III collagen are disclosed in U.S. Pat. Nos. 4,973,666 and 5,140,103. However, both these patents are restricted to collagen fragments containing the cross-linker 3-hydroxypyridinium, whereas the present invention does not rely on the presence or absence of this particular cross-linking structure. Furthermore, the above-mentioned assays require tedious and complicated purifications from urine of collagen fragments containing 3-hydroxypyridinium to be used for the production of antibodies and for antigens in the assays.

At present very few clinical data using the approach described in U.S. Pat Nos. 4,973,666 and 5,140,103 are available. Particularly, no data concerning the correlation between the urinary concentration (as determined by methods described in the above-mentioned patents) of 3-hydroxypyridinium containing telopeptides of type I collagen and the actual bone loss (as determined by repeated measurements by bone densitometry) are published. The presence of 3-hydroxypyridinium containing telopeptides in urine requires the proper formation in bone tissue of this specific cross-linking structure at various times before the bone resorbing process. Very little information on these processes is available and the present invention seeks to circumvent this dependance of the correct formation of the cross-linking structure. Furthermore, preliminary data indicate that in one embodiment of the present invention a major fraction of the molecules reactive in the assay has a molecular weight of more than 4,000 daltons. On the contrary, only molecules with a molecular weight below 2,000 daltons are identified in urine with the monoclonal antibody used in the assay; Hanson et al., *Journal of Bone and Mineral Research* 7:1251–1258 (1992). This demonstrates that the method according to the present Invention has a very different profile of reactivities, i.e. it detects very different molecules, compared to methods described in the two above-mentioned U.S. patents.

None of the above researcher have reported specifically assaying a crosslinkable collagen fragment that is naturally produced in vivo upon collagen degradation, as in the present invention.

GB patent application No. 2,205,643 reports that the degradation of type III collagen in the body can be quantitatively determined by measuring the concentration of an N-terminal telopeptide from type III collagen in a body fluid. This method does not relate to methods employing antibodies reactive with specific, low molecular weight sequences around crosslinkable structures. Instead, the method uses antibodies generated to N-terminal telopeptides released by bacterial collagenase degradation of type III collagen, said telopeptides being labelled and used in the assay.

There are a number of reports indicating that collagen degradation can be measured by quantitating certain procollagen peptides. Propeptides are distinguished from telopeptides and alpha-helical region of the collagen core by their location in the procollagen molecule and the timing of their cleavage in vivo; see U.S. Pat. Nos. 4,504,587; 4,312,853; Pierard et al., *Analytical Biochemistry* 141:127–136 (1984); Niemela, *Clin. Chem.* 31/8:1301–1304 (1985); and Rohde et al., *European Journal of Clinical Investigation* 9:451–459 (1979).

U.S. Pat. No. 4,778,768 relates to a method of determining changes occurring in articular cartilage involving quantifying proteoglycan monomers or antigenic fragments thereof in a synovial fluid sample. This US patent does not relate to detecting collagen fragments derived from degraded collagen.

Dodge, *J. Clin, Invest.* 83;647–661 (1981) discloses methods for analyzing type II collagen degradation utilizing a polyclonal antiserum that specifically reacts with unwound alpha-chains and cyanogen bromide-derived peptides of human and bovine type II collagens. Contrary to the present invention the degradation products of collagen were not detected in a body fluid, but histochemically by staining of cell cultures, i.e. by "in situ" detection. The main difference between Dodge and the present invention is that Dodge measures type II collagen degradation in situ. By "in situ" is meant a determination carried out in the cells or tissue in which the degradation taken place. There is quite a fundamental difference between this determination and a method based upon tracing a marker in vitro, e.g. in the urine.

None of these references specify the structures of particular telopeptide or alpha-helical degradation products that could be measured to determine the amount of degraded fibrillar collagen in vivo.

SUMMARY OF THE INVENTION

The present invention is based on the discovery of the presence of particular collagen fragments in body fluids of patients and normal human subjects. The collagen fragments are generated upon collagen degradation and are partly characterized by the presence of potential sites for cross-linking, e.g. by the presence of lysine or hydroxylysine (Kühn, K., *Immunochemistry of the Extracellular Matrix* 1:1–29 (1982)). It is believed that a fraction of the collagen fragments measured by the assays embodied in the present invention are normally covalently linked in vivo to other peptide fragments through different, unidentified or already identified cross-links.

The method of the present invention may be used for determination of the degradation of human collagen of type I, II, and III.

The present invention provides a method of assessing the degradation of collagen based on a determination of the presence and quantity of a particular class of collagen fragments produced in vivo upon collagen degradation; and a comparison of the detected collagen fragments to those of a predetermined standard developed by measuring the same class of collagen fragments in normal individuals, i.e. individuals not afflicted with a disorder affecting collagen metabolism, said individuals being sex- and age-matched with the subjects being tested.

The present invention uses antibodies immunoreactive with synthetic peptides without these cross-linking structures. Accordingly, it is believed that collagen fragments (corresponding to the synthetic peptides) with or without actual cross-links, but with crosslinkable sites, are measured in the assays embodied in the present invention.

In a preferred embodiment, the method is based on the competitive binding of collagen fragments in body fluids and of synthetic peptides essentially derived from collagen to immunological binding partners.

The present invention provides new and very simple procedures for the detection (qualitative and quantitative) of collagen fragments generated upon collagen degradation.

For purposes of the present invention, as disclosed and claimed herein, the following terms are as defined below:

"Antibody": A monoclonal or polyclonal antibody or immunoreactive fragment thereof (i.e. capable of binding the same antigenic determinant), including—but not limited to—Fab, Fab', and F(ab')2 fragments.

"Crosslinkable sites": loci in collagen telopeptide or helix amino acid sequences containing lysine or hydroxylysine residues which can form cross-links with telopeptides or helical amino acid sequences of other collagen molecules in vivo.

"Crosslinkable peptides": peptides containing a fragment of the collagen sequence including at least one crosslinkable site.

Test kit: A combination of reagents and instructions for use in conducting an assay.

"Essentially derived" (about structures): Structures with similar antigenicity, i.e. with an ability, above the level of a non-related peptide, to inhibit the binding of any of the mentioned synthetic peptides to an antibody immunoreactive with said synthetic peptide.

It is contemplated that the method may also be used for assaying collagen fragments in animal body fluids, e.g. for determination of the collagen metabolism. It also can be used during clinical testing of new drugs to assess the impact of these drugs on collagen metabolism.

More specifically, the present invention relates to methods for assaying collagen fragments by the use of synthetic peptides corresponding to the above-mentioned sequences of collagen. Generally, these synthetic peptides will have fewer amino acid residues than the entire collagen molecule, often they will have fewer than 10 amino acids. Also, the synthetic peptides, corresponding to molecules present in body fluids, e.g. urine, will have potential sites for cross-linking, preferably lysine or hydroxylysine, incorporated in the structure.

The present invention comprises the determination of collagen fragments by the use of antibodies which are immunoreactive with the above-mentioned synthetic peptides, said peptides each having a sequence derived from collagen fragments having crosslinkable sites.

The invention also includes cell lines (e.g. hybridomas) that produce monoclonal antibodies immunoreactive with the above-mentioned synthetic peptides. The invention further includes monoclonal antibodies produced by the fused cell hybrids, and those antibodies (as well as binding fragments thereof, e.g. Fab) coupled to a detectable marker. Examples of detectable markers include, but are not limited to, enzymes, chromophores, fluorophores, coenzymes, enzyme inhibitors, chemiluminescent materials, paramagnetic metals, spin labels and radioisotopes.

The methods of the invention involve quantitating in a body fluid the concentration of particular collagen fragments derived from collagen degradation. In a representative assay, collagen fragments in the patient's body fluid and a synthetic peptide immobilized on a solid surface are contacted with an immunological binding partner which is immunoreactive with the synthetic peptide. Suitable body fluids are e.g. human urine, blood, serum, plasma and synovial fluid. It is contemplated that the method may also be used e.g. on saliva and sweat. The body fluid may be used as it is, or it may be purified prior to the contacting step. This purification step may be accomplished using a number of standard procedures, including, but not limited to, cartridge adsorption and elution, molecular sieve chromatography, dialysis, ion exchange, alumina chromatography, hydroxyapatite chromatography, and combinations thereof.

The present invention is based on the discovery of simple procedures for quantitation of collagen fragments in body fluids. In a representative procedure, synthetic peptides containing potential sites for cross-linking, are used for the raising of antibodies and subsequently incorporated in the assay for quantitation of collagen fragments generated in vivo by collagen degradation.

The invention also includes test kits useful for quantitating in a body fluid the amount of collagen fragment derived from the degradation of collagen. The kits comprise at least one immunological binding partner, e.g. a monoclonal or polyclonal antibody specific for a peptide derived from the degradation of collagen. If desired, the immunological binding partner of the test kit may be coupled to detectable markers such as the ones described above.

The invention is described in more detail below. Reference is made to the appended drawings.

DETAILED DESCRIPTION AND BEST MODE OF CARRYING OUT THE INVENTION

Figure 1:
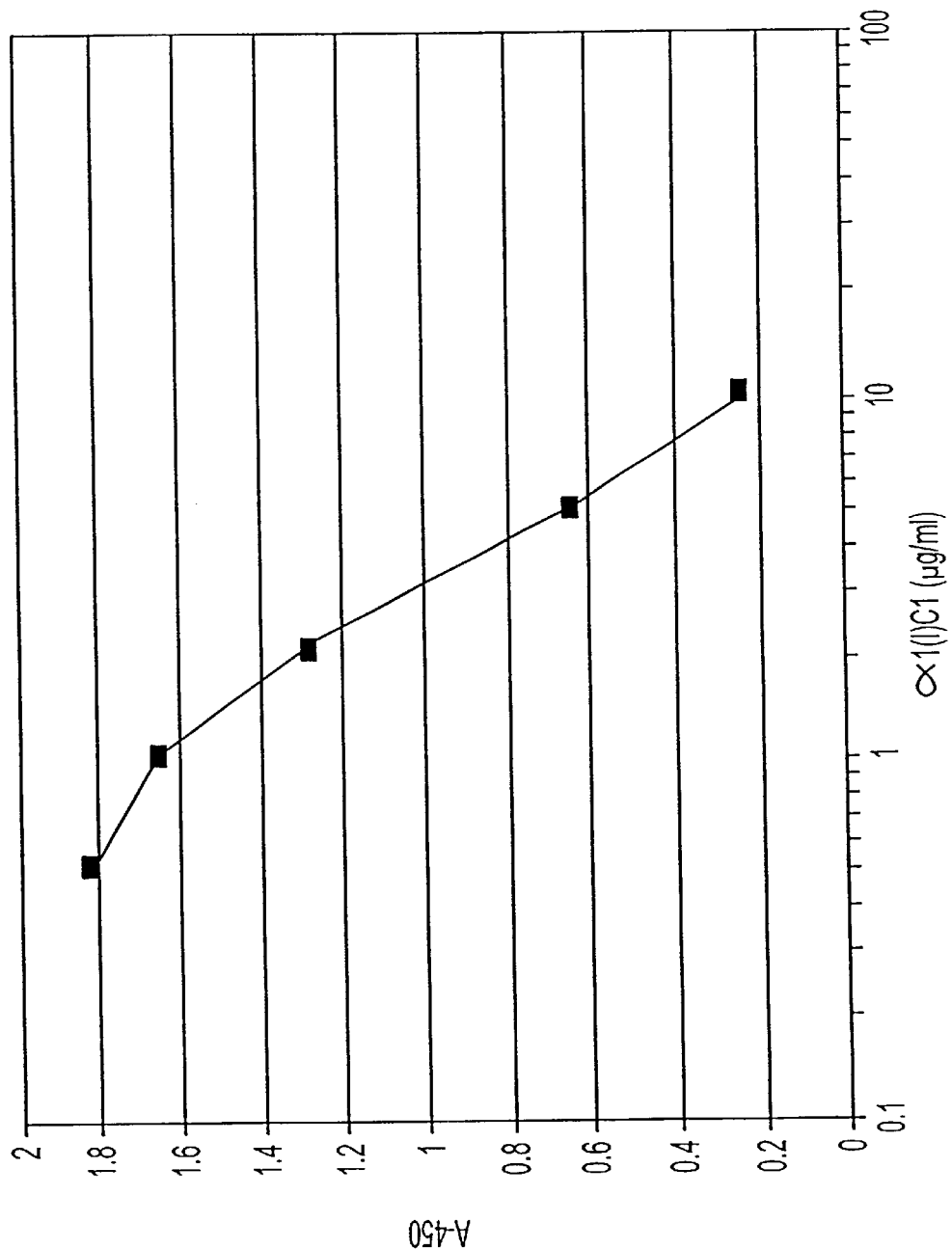
FIGS. 1, 2 and 3 are typical standard curves for the α1(I)C1 immunoassay (FIG. 1), the a1(I)N1 immunoassay (FIG. 2) and the α2(I)N1 immunoassay (FIG. 3) to be described in more detail in the examples.

In a preferred embodiment of the method according to the invention, the assaying of type I, II and III collagen fragments in urine is performed by an inhibition ELISA (enzyme linked immunosorbent assay) by metering off a sample of urine and contacting the sample with a synthetic peptide having a sequence derived from collagen and with an antibody, which is immunoreactive with the synthetic peptide. The synthetic peptide is immobilized on a solid support. The antibody is raised against the synthetic peptide.

The combined reagents and sample are incubated, and a peroxidase-conjugated (revealing) antibody is added. After another incubation, a peroxidase substrate solution is added. Following short final incubation, the enzyme reaction is stopped, and the absorbance is measured at 450 nm and compared with a standard curve obtained with standard solutions by the same procedure.

Synthetic peptides are used for the preparation of standards. The concentration of synthetic peptide in a stock solution of the relevant synthetic peptide is determined by quantitative amino acid determination. A two-fold dilution of the stock solution is prepared and subsequently used for the construction of the standard curve in the inhibition ELISA.

Preparation of Synthetic Peptides

The preparation of synthetic peptides may be performed according to procedures well known in the art, e.g. by solid-phase peptide synthesis techniques commonly described as "Merrifield synthesis". Also classical solution phase techniques may be used. Sequences of interest include potential sites for cross-linking (see for example Kühn, K., in *Immunochemistry of the Extracellular Matrix* 1:1–29 (1982), Eyre, D. R., *Ann. Rev. Biochem.* 53:717–48 (1984), or U.S. Pat. No. 5,140,103). Examples of such peptides sequences are given in table 1 below.

Regarding the synthetic peptides, it is possible to omit (or add) one or more amino acid residues from (or to) the crosslinkable site sequences without substantial loss of the ability to (a) raise antibodies recognizing the corresponding native collagen fragment or (b) inhibit the bindings of such antibodies to the native fragment. It is possible to use longer collagen fragments and/or chimeric peptides to raise the antibodies and, in principle, it is not necessary to use the same peptide as the immunogen and the competitor in the assay.

```
Collagen type I
Potential sites
in telopeptides: N                               C
α1 (I) N-term. Asp-Glu-Lys-Ser-Thr-Gly-Gly (α1(I)N1) (SEQ. ID
NO: 1)
α1 (I) C-term. Glu-Lys-Ala-His-Asp-Gly-Gly-Arg (α1(I)C1) (SEQ.
ID NO: 2)
α2 (I) N-term. Gln-Tyr-Asp-Gly-Lys-Gly-Val-Gly (α2(I)N1) (SEQ.
ID NO: 3)
α2 (I) C-term. no potential sites Potential sites
in helix:
α1 (I) (near N) Gly-Met-Lys-Gly-His-Arg (SEQ. ID NO: 4)
α1 (I) (near C) Gly-Ile-Lys-Gly-His-Arg (SEQ. ID NO: 5)
α2 (I) (near N) Gly-Phe-Lys-Gly-Ile-Arg (SEQ. ID NO: 6)
α2 (I) (near C) Gly-Leu-Pro-Gly-Leu-Lys-Gly-His-Asn (SEQ. ID NO:
7)

Potential sites
in telopeptides: N                               C
α1 (II) N-term. Pro-Gly-Pro-Lys-Gly-Glu (SEQ. ID NO: 8) Gly-Gln-
Lys-Gly-Glu-Pro (SEQ. ID NO: 9) Gly-Asp-Ile-Lys-Asp-Ile-Val (SEQ.
ID NO: 10)
α1 (II) C-term. Glu-Lys-Gly-Pro-Asp (SEQ. ID NO: 11)

Potential sites
in helix:
α1 (II) (near N) Gly-Val-Lys (SEQ. ID NO: 12) Pro-Gly-Val-Lys-
Gly (SEQ. ID NO: 13)

Potential sites
in telopeptides:  N                              C
α1 (III) N-term. Asp-Val-Lys-Ser-Gly-Val (SEQ. ID NO: 14)
α1 (III) C-term. Glu-Lys-Ala-Gly-Gly-Phe-Ala (SEQ. ID NO: 15)
```

-continued

```
in helix:
α1 (III) (near N) Gly-Phe-Pro-Gly-Met-Lys-Gly-His-Arg (SEQ. ID
NO: 16)
α1 (III) (near C) Gly-Ala-Ala-Gly-Ile-Lys-Gly-His-Arg (SEQ. ID
NO: 17)
```

Preparation of Antibodies

The methods for preparation of both monoclonal and polyclonal antibodies are well known in the art. For example, see Campbell, A. M., *Laboratory Techniques in Biochemistry and Molecular Biology*, Vol. 13 (1986). It is possible to produce antibodies to synthetic peptides by immunization. However, because of the relatively small molecular weight of these compounds it is preferred that the hapten be conjugated to a carrier molecule. Suitable carrier molecules include, but are not limited to, bovine serum albumin, thyroglobulin, ovalbumin, tetanus toxoid, and keyhole limpet hemocyanin. The preferred carrier is bovine serum albumin. To present the hapten in its most immunogenic form to the antibody producing cells of the immunized animal a number of alternative coupling protocols can be used. Suitable procedures include, but are not limited to, glutaraldehyde, carbodiimide, and periodate. Preferred binding agents are glutaraldehyde and carbodiimide.

The preparation of antibodies is carried out by conventional techniques including immunization with collagen fragments or synthetic peptides conjugated to a carrier. To improve the immunogenicity it is preferred that the immunogen be mixed with an adjuvant before injection. Examples of adjuvants include, but are not limited to, aluminum hydroxide, Freund's adjuvant, and immune-stimulating complexes (ISCOMs). ISCOMs can be made according to the method described by Morein, B. et al., *Nature* 308:457–460 (1984).

Either monoclonal or polyclonal antibodies to the hapten carrier molecule can be produced. For the production of monoclonal antibodies it is preferred that mice are immunized. Spleen cells from the immunized mouse are harvested, homogenized, and thereafter fused with cancer cells in the presence of polyethylene glycol to produce a cell hybrid which produces monoclonal antibodies specific for peptide fragments derived from collagen. Suitable cancer cells include, but are not limited to, myeloma, hepatoma, carcinoma, and sarcoma cells. Detailed descriptions of the production of monoclonal antibodies are provided in Goding, J. W., in *Monoclonal Antibodies: Principles and Practice*, (1986). A preferred preliminary screening protocol comprises the use of synthetic peptides conjugated to a carrier and coated onto the solid surface of a microtitre plate.

For the preparation of polyclonal antibodies, which are reactive with peptide fragments derived from collagen, different animal species can be immunized. Suitable species include, but are not limited to, chicken, rabbit and goat. Chicken and rabbit are preferred.

Antibody fragments are prepared by methods known in the art (see E. Ishikawa, *J. of Immunoassay* 3:209–327, 1983).

Conduct of Immunoassays

Accordingly, by utilization of an immunoassay with the antibodies prepared as above it is possible to assay a biological fluid sample without prior fractionation or hydrolysis. The specificity for the desired collagen in the biological fluid is supplied by the antibody in combination with the use of a synthetic peptide (against which the antibody was raised or in any event with which the antibody is immunochemically reactive) in the assay construction. The immunoassays themselves are conducted using any procedure selected from the variety of standard assay protocols generally known in the art. As it is generally understood, the assay is constructed so as to rely on the interaction between the specific immunological binding partner and the desired analyte for specificity and to utilize some means to detect the complex formed by the analyte and the immunological binding partner. The immunological binding partner may be complexed to a solid support and used as a capture immunological binding partner for the analyte. This protocol may be run in a direct form, wherein the formation of analyte/immunological binding partner complex is detected, e.g. by a fluorescent, radioactive or enzymatic label, or it may be run in a competitive format wherein a labelled standard competes with the analyte for the immunological binding partner. The format may also be constructed as an agglutination assay or the complex may be precipitated by addition of a suitable precipitant to the reaction mixture. The specific design of the immunoassay protocol is open to a wide variety of choice, and the number of clinical assay devices and protocols available in the art is multitudinous. For a variety of such protocols, see U.S. Pat. No. 5,001,225.

The antibodies and revealing reagents for the conduct of an immunoassay using standard detection protocols, for example radioisotope labelling, fluorescent labelling or ELISA, either in a direct or competitive format, may conveniently be supplied as kits which include the necessary components and instructions for the assay. In one embodiment of the invention such a kit includes a microtiter plate coated with a relevant synthetic peptide, standard solutions for preparation of standard curve, a urine control for quality testing of the analytical run, rabbit antibodies reactive with the above-mentioned synthetic peptide, anti-rabbit immunoglobulins conjugated to peroxidase, a substrate solution, a stopping solution, a washing buffer and an instruction manual.

Since immunoassays can be constructed using antibodies and specific synthetic peptides, the ratios of the corresponding collagen fragment sequences in an appropriate biological fluid can be determined as well as their individual levels and their total. Thus, the assay can be designed to include antibodies which will result in determination of several native peptide sequences or determination of a single peptide sequence, or any desired combination thereof.

In addition to the use of the herein specified peptides as indicators of bone resorption, bone metabolic balance is advantageously determined by the substantially simultaneous determination of a marker of the formation of bone in the same or other appropriate biological fluid from the same individual. "Substantially simultaneous" means the same day, preferably within 4 hours. For example such markers include osteocalcin (also known as bone GLA protein of BGP), procollagen type I, bone alkaline phosphatase and total alkaline phosphatase. Suitable methods for the determination of these markers can be found, for example, in Delmas, P. D., et al., *J. Bone Min. Res.* 1:333–337 (1986).

The assay of the present invention which provides an index to determination of the metabolic status of tissues, which generate collagen-derived peptides when degradation occurs, are useful ^ in a variety of contexts. First, when considering the degradation of type I collagen, the assays are methods to assess an abnormal condition of a subject by indicating, for example, excessive bone resorption. This may show the presence of an osteoporotic condition or the metastatic progress of a malignancy. Other conditions characterized by excessive bone resorption include Paget's disease and hyperparathyroidism. Likewise, a number of other disease states involving connective tissue may be monitored by determination of the degradation of collagen. Examples are collagen type II degradation associated with rheumatoid arthritis and osteoarthritis and collagen type III degradation in vasculitis syndrome. Since the condition of the subject can be monitored continuously, application of these assays can also be used to monitor the progress of therapy administered to treat these or other conditions. Further, the assays can be used as a measure of toxicity, since the administration of toxic substances often results in tissue degradation.

Thus the assays may be applied in any situation wherein the metabolic condition of collagen tissues can be used as an index of the condition, treatment, or effect of substances directly administered to the subject or to which the subject is exposed in the environment.

The following examples are intended to illustrate, but not to limit the invention.

EXAMPLE 1

Immunoassays for Specific Peptide Sequences in Urine

Three peptides ($\alpha 1(I)C1$, $\alpha 1(I)N1$, and $\alpha 2(I)N1$) (see Table 1, p. 13) prepared by solid-phase techniques are used for the preparation of immunogens. For immunization, the peptides are covalently attached to bovine serum albumin using glutaraldehyde reagents and methods well known in the art. Both monoclonal and polyclonal antibodies are raised against the peptides. For production of monoclonal antibodies, Balb/c mice are immunized with peptide-BSA conjugates, and hybridoma cell lines are prepared using standard techniques after fusion of cells from the spleen or lymph nodes with Ag8 myeloma cells. Polyclonal antibodies are raised in rabbits and chicken. Screening of both antisera and hybridoma cell media were performed by ELISA using microtiter plates coated with the appropriate peptide-gelatin conjugate prepared using carbodiimide reagents and methods well known in the art.

Figure 2:
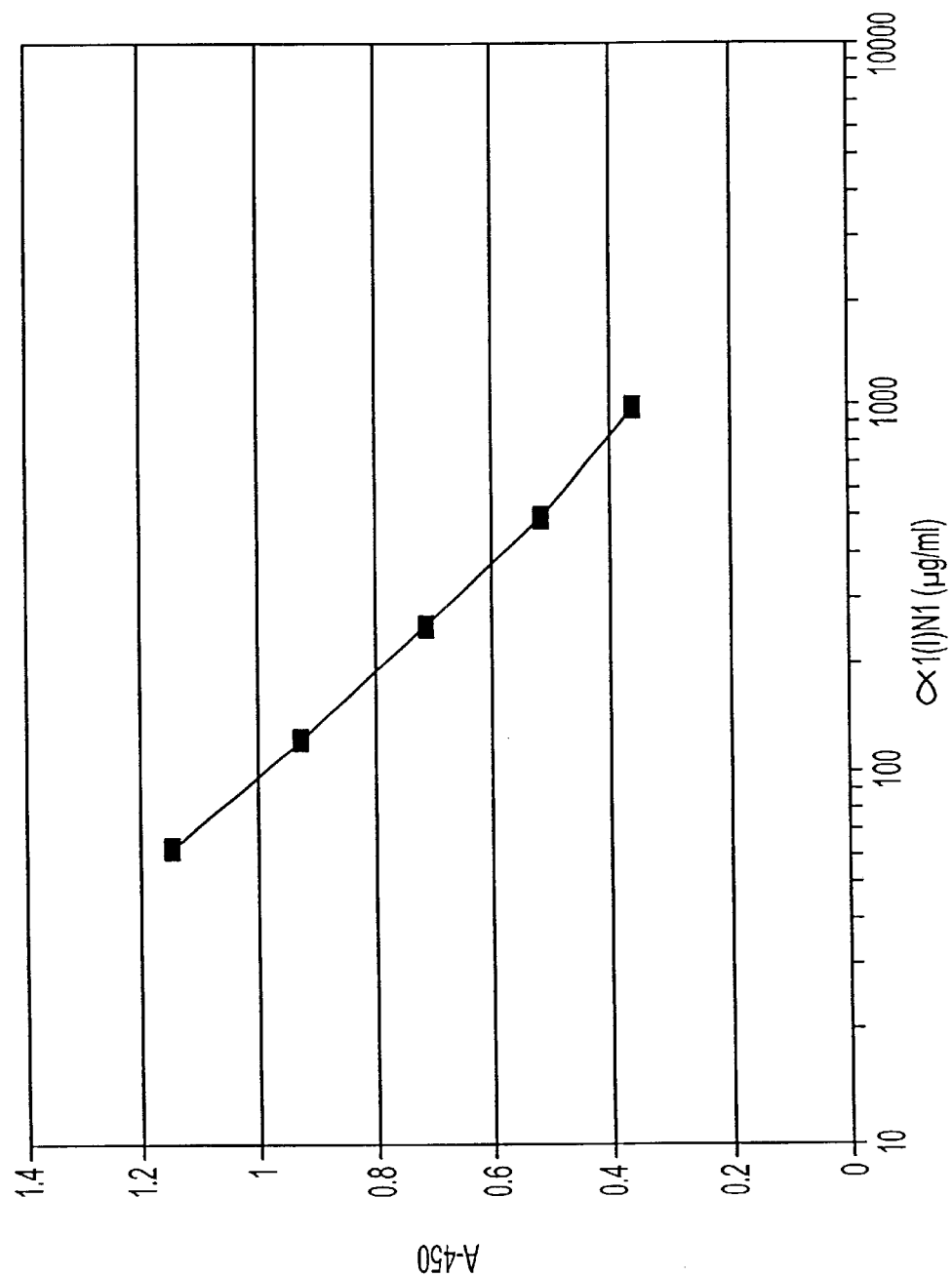
Figure 3:
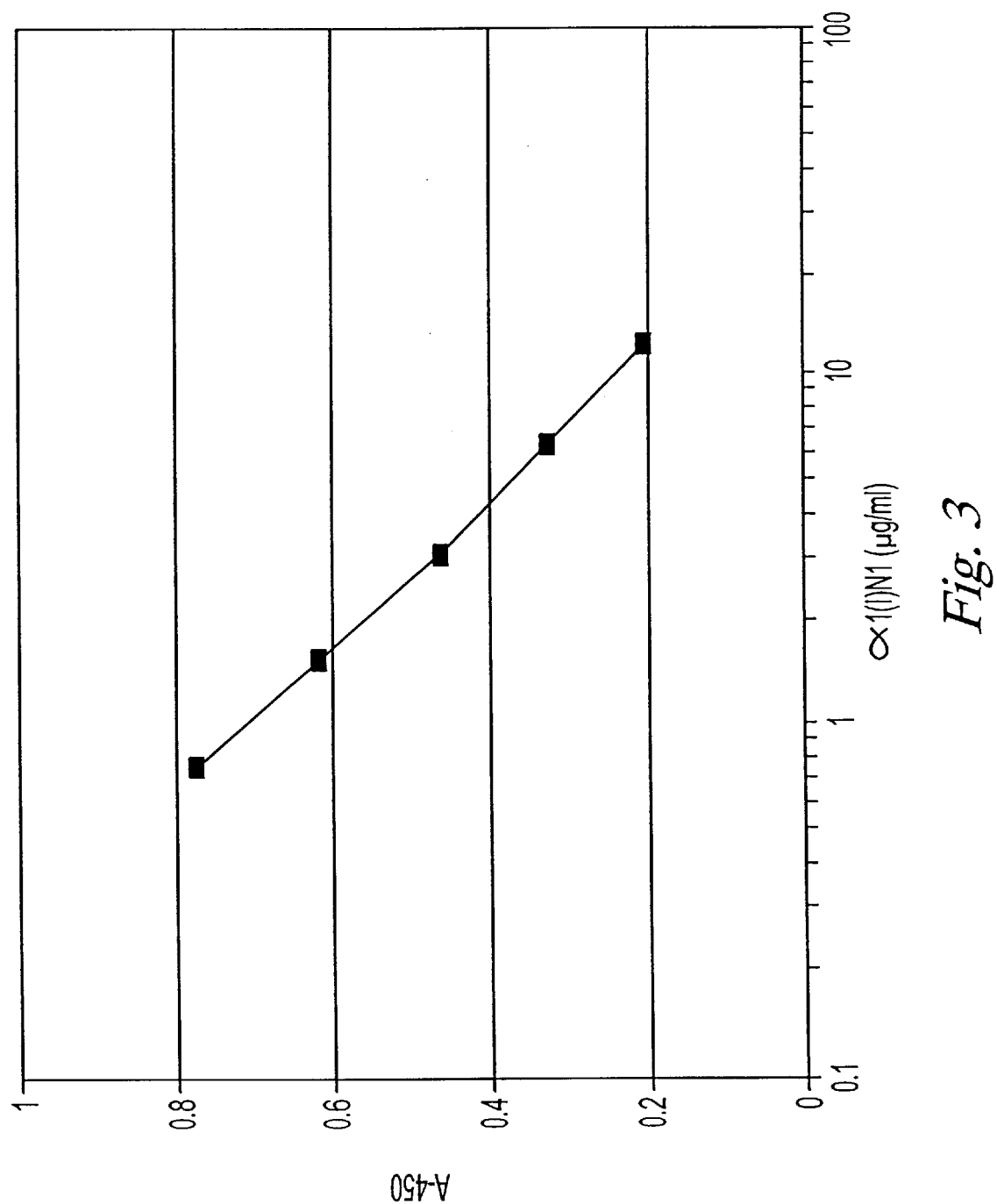

Assays for three of the peptide sequences ($\alpha 1(I)C1$ $\alpha 1(I)N1$, and $\alpha 2(I)N1$) in urine are performed by an inhibition ELISA as follows:

Urine samples (10 or 25 1) possibly containing collagen fragments or solutions containing 0.05–15 g peptide/ml as reference standards, respectively, are added to 75 1 of immunological binding partners for the peptides diluted 1:5,000–1:20,000 in phosphate buffered saline containing 0.1% Tween-20 detergent (PBS-T) and including 0.1% (w/v) of BSA. Each sample is prepared in duplicate in flat-bottomed, 96-well microtiter plates previously coated with gelatine conjugate containing the appropriate peptide. After 60 minutes, the plates are washed with PBS-T (3 times) and the bound antibodies are detected by standard techniques with a horse radish peroxidase labelled antibody prepared against the species of the primary antibody. Peroxidase substrate is added and the color development is measured at 450 nm in an automated microtiter plate reader after stopping the enzyme reaction using 1 M H3PO4. Samples containing the analyte decrease the binding of primary antibody to the immobilized peptide in the plate and thus have a reduced color concentration. The amount of analyte in the sample is quantified with reference to previously established curves from standards included on each plate computed using log-lin plots. FIGS. 1, 2 and 3 show typical standard curves for the $\alpha 1(I)C1$ immunoassay (FIG. 1), $\alpha 1(I)N1$ immunoassay (FIG. 2), and $\alpha 2(I)N1$ immunoassay (FIG. 3).

EXAMPLE 2

Correlation to Pyridinolin Determination on HPLC

On a number of unselected urine samples the concentration of total pyridinolin (HPLC method, see for example Uebelhart, D., *Bone and Mineral* 8:87–96 (1990)) was measured. Values obtained in this HPLC system were correlated to the values obtained in two immunoassays ($\alpha 1(I)$ C1 peptide and $\alpha 1(I)N1$ peptide).

Figure 4:
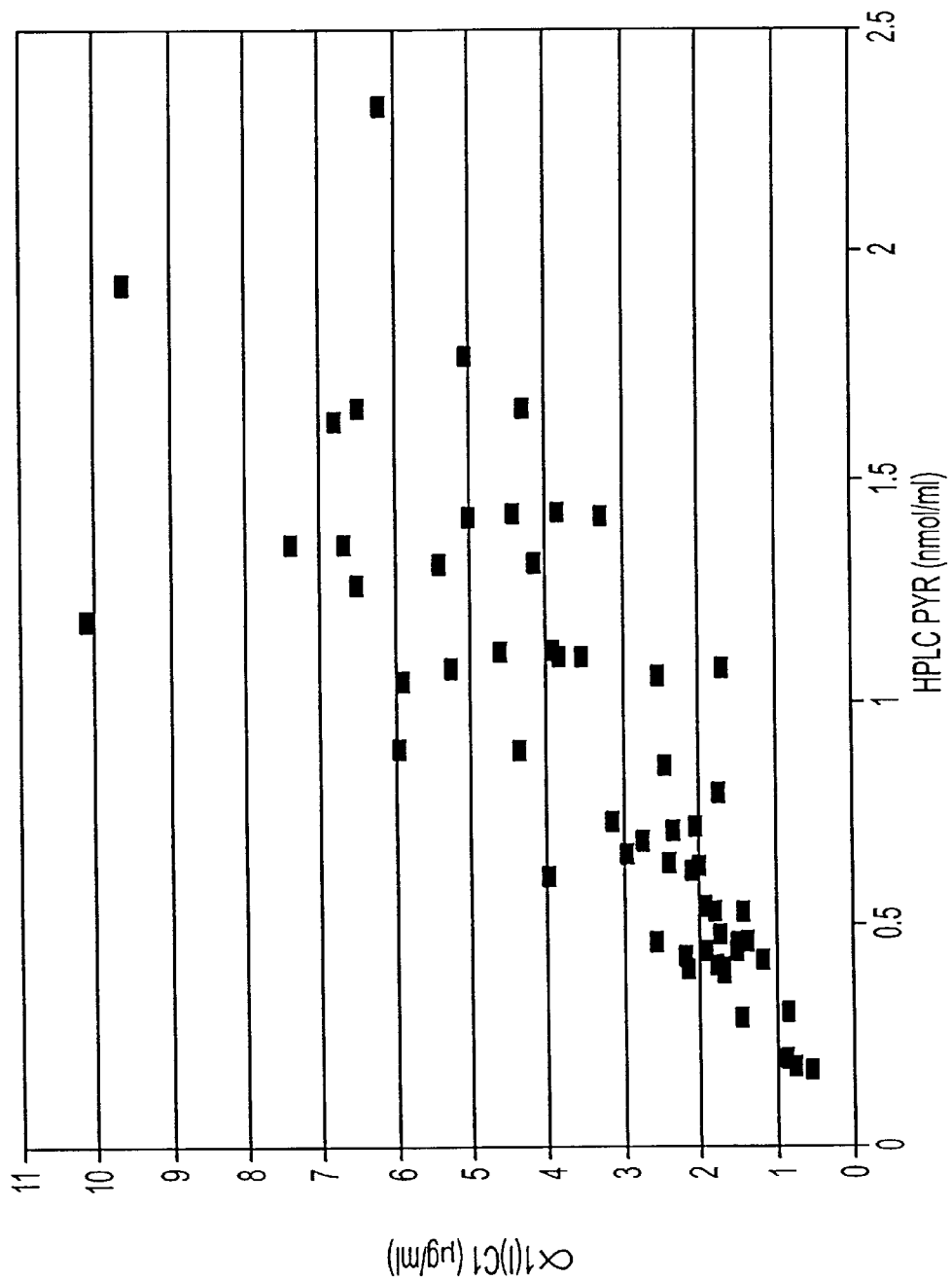
FIG. 4 shows the correlation between total pyridinolin (HPLC) and the α1(I)C1 immunoassay.

FIG. 4 shows the correlation between total pyridinolin (HPLC) and $\alpha 1(I)C1$ immunoassay (n=59). The correlation calculated by linear regression analysis is r=0.80.

Figure 5:
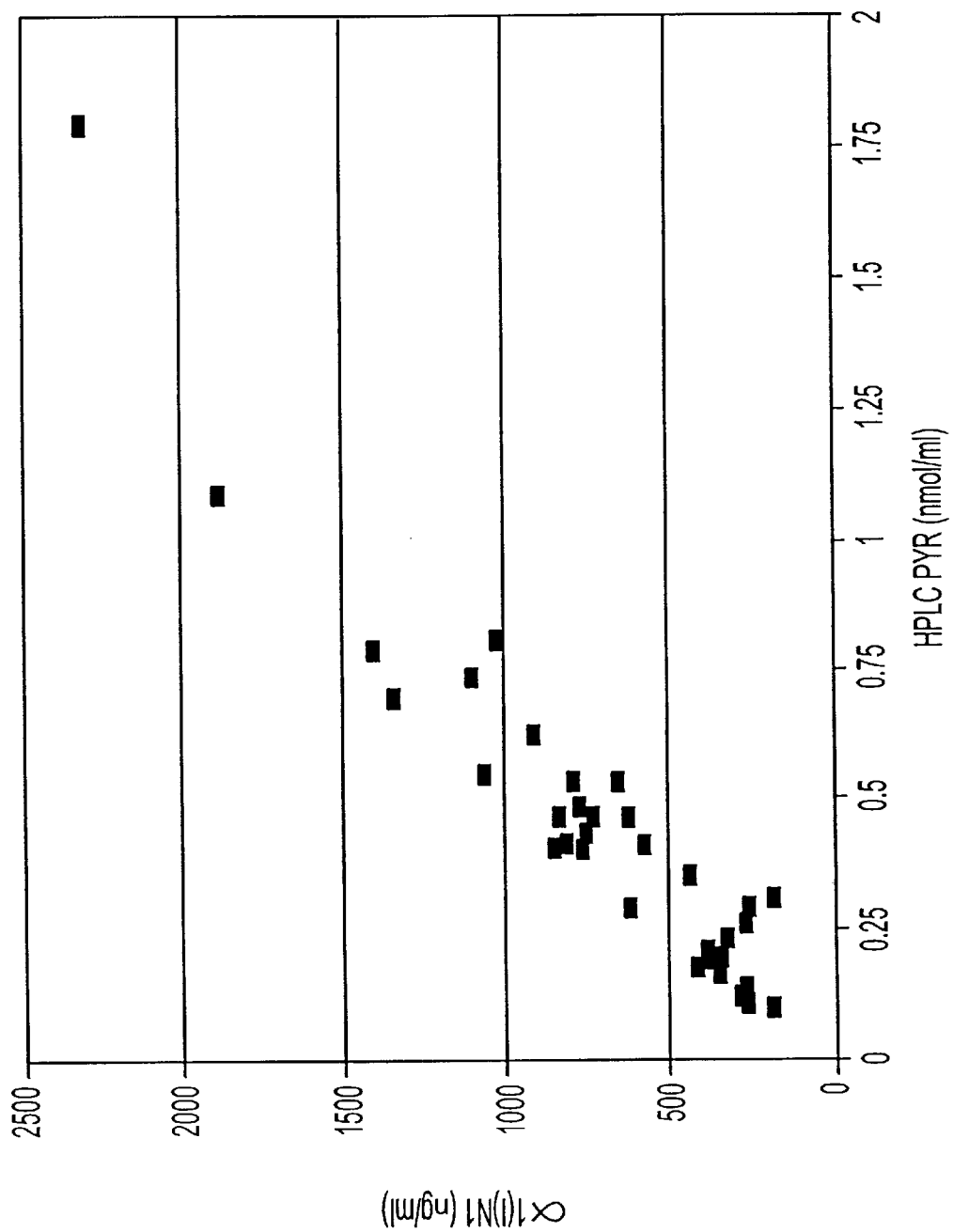
FIG. 5 shows the correlation between total pyridinolin (HPLC) and the α1(I)N1 immunoassay.

FIG. 5 shows the correlation between total pyridinolin (HPLC) and $\alpha 1(I)N1$ immunoassay (n=36). The correlation calculated by linear regression analysis is r=0.95.

EXAMPLE 3

Clinical Results

The immunoassay procedure (using the $\alpha 1(I)C1$ peptide) set forth in Example 1 was applied to urine samples from different individuals, and the amount of analyte was quantitated. The values obtained were related to the level of urinary creatinine in the urine sample as is commonly done for urine assays. The values obtained for normal, age-matched women (premenopausal and postmenopausal) are shown in Table 2.

TABLE 2

Measurement of $\alpha 1(I)C1$ peptide in urine samples from normal, age-matched women (premenopausal and postmenopausal)

| Group | $\alpha 1(I)C1$ peptide (g/mol creatinine) |
| --- | --- |
| Premenopausal (n = 104) | 0.263 ± 0.143 |
| Postmenopausal (n = 180) | 0.426 ± 0.190 |

Figure 6:
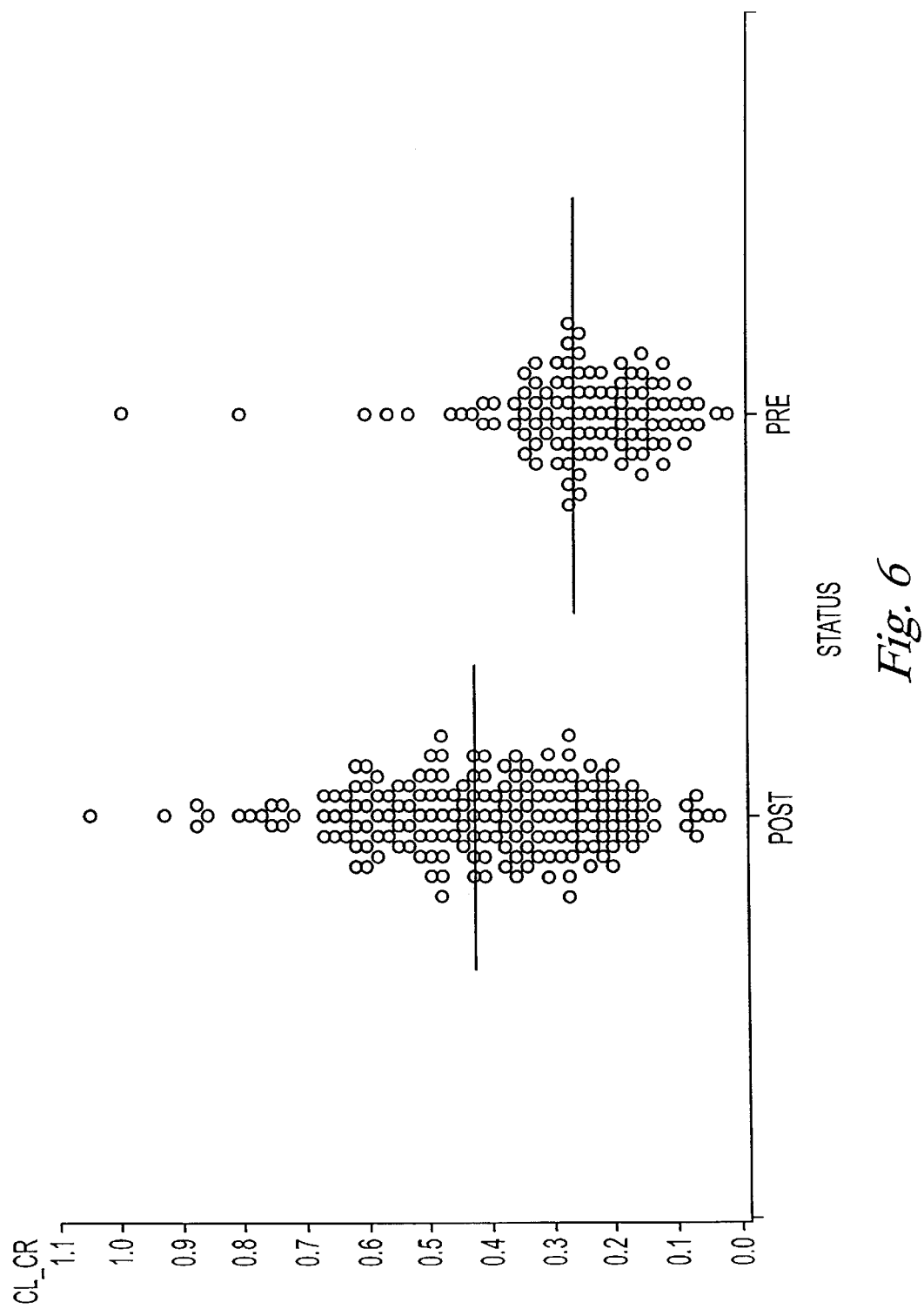
FIG. 6 shows the individual values of the measurement of α1(I)C1 peptide in urine samples from normal, age-matched women.

For individual values see FIG. 6.

The difference between the premenopausal and the postmenopausal values is highly significant (P<0.0001).

The z-score of a quantitative test procedure shows the ability of the procedure to distinguish between two populations. Table 3 below shows the z-score of the IC1 immunoassay and the state of the art measurement of pyridinolin on HPLC when applied to the same set of urine samples from normal, age-matched premenopausal (n=104) and postmenopausal women (n=180).

TABLE 3

Z-scores obtained for two different test procedures (total pyridinolin (HPLC) and α1(I)C1 immunoassay) when applied to urine samples from normal, age-matched women (premenopausal and postmenopausal)

| Test procedure | Z-score |
| --- | --- |
| α1(I)C1 immunoassay | 1.14 |
| Total pyridinolin (HPLC) | 1.25 |

As can be seen from Table 3, the abilities of the two methods to distinguish between patient populations are approximately alike.

For an assay to be used as an index of bone resorption it is very important to be able to measure the impact of a hormone replacement therapy (HRT). Table 4 shows the results from the α1(I)C1 immunoassay in such a study.

TABLE 4

Measurement of urine samples from women on a hormone replacement therapy and placebo in the α1(I)C1 immunoassay. Values given as percent of $t = 0$

| Group | α1(I)C1 peptide ($\mu$g/mol creatinine) $t = 0$ | $t = 12$ months |
| --- | --- | --- |
| HRT (n = 92) | 0.457 ± 0.176 | 0.176 ± 0.103 |
| Placebo (n = 45) | 0.459 ± 0.209 | 0.402 ± 0.187 |

Figure 7:
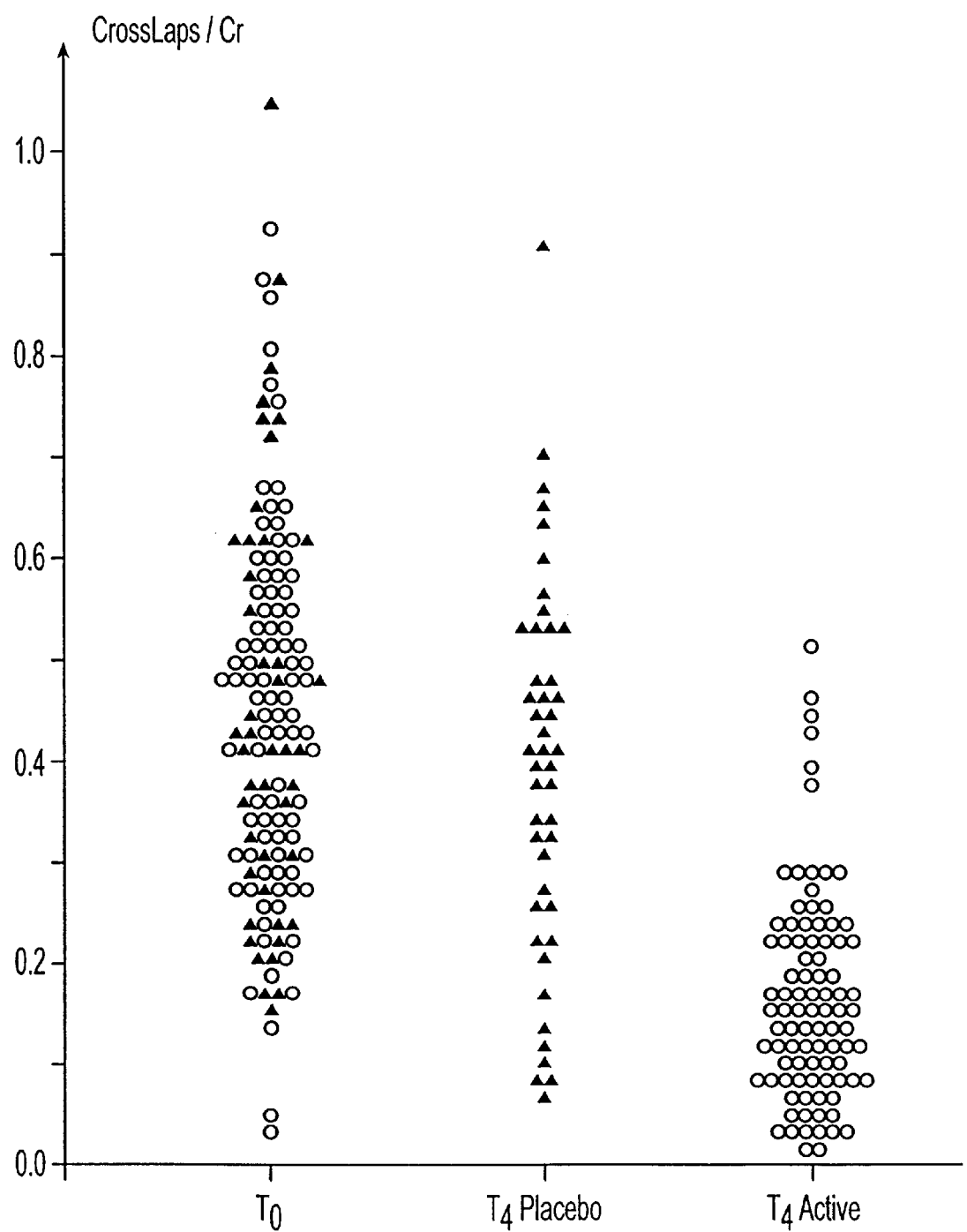
FIG. 7 shows the individual values of the measurement of urine samples from women on a hormone replacement therapy and placebo in the α1(I)C1 immunoassay.

For individual values see FIG. 7.

A highly significant drop in the group receiving HRT is seen after 12 months (P<0.001).

All cited patents, patent applications and literature are incorporated by reference in their entirety. In case of conflict, however, the present disclosure controls.

The invention has been described above by reference to specific embodiments. It will be apparent to those skilled in the art, however, that many additions, deletions and modifications are possible without departing from the spirit of the invention as claimed below.

---

What is claimed is:

1. A method of assaying Type I collagen fragments in a body fluid, comprising:
   (a) contacting a sample of the body fluid with a synthetic peptide immobilized on a solid support and with an immunological binding partner which is immunologically reactive with said immobilized synthetic peptide, wherein the collagen fragments compete with said synthetic peptide for binding with the immunological binding partner; and
   (b) quantifying the amount of collagen fragments in the body fluid by measuring the amount of binding of said immunological binding partner with said synthetic peptide; wherein
   said immunological binding partner is immunologically reactive with a peptide immobilized on a solid support and consisting essentially of the amino acid sequence Gln-Tyr-Asp-Gly-Lys-Gly-Val-Gly (SEQ. ID NO: 3); and
   said immobilized synthetic peptide contains no collagen cross-link structure but spans a region of a sequence of Type I collagen at which in nature a cross-link structure would form, and is immunologically reactive with said immunological binding partner.

2. The method of claim 1, wherein said immobilized synthetic peptide consists of fewer than 10 amino acids.

3. The method of claim 1 or 2, wherein the immobilized synthetic peptide consists essentially of the amino acid sequence Gln-Tyr-Asp-Gly-Lys-Gly-Val-Gly (SEQ. ID NO: 3) or consists essentially of the sequence Gln-Tyr-Asp-Gly-Lys-Gly-Val-Gly (SEQ. ID NO: 3) modified by the addition or omission of one or more amino acids while retaining the ability to raise antibodies recognising a corresponding native collagen fragment or to inhibit the binding of such antibodies to a corresponding native collagen fragment.

4. The method of claim 1, wherein said immunological binding partner is a whole antibody.

5. The method of claim 4, wherein said antibody is a monoclonal antibody.

6. A test kit for assaying Type I collagen fragments in a body fluid, comprising:

(a) an immunological binding partner which is immunologically reactive with a synthetic peptide immobilized on a solid support and consisting essentially of the amino acid sequence Gln-Tyr-Asp-Gly-Lys-Gly-Val-Gly (SEQ. ID NO: 3); and (b) a synthetic peptide immobilized on a solid support, said synthetic peptide containing no collagen cross-link structure but spanning a region of a sequence of Type I collagen at which in nature a cross-link structure would form, and being immunologically reactive with said immunological binding partner.

7. The kit of claim 6, wherein said immobilized synthetic peptide consists of fewer than 10 amino acids.

8. The kit of claim 6 or 7, wherein the immobilized synthetic peptide consists essentially of the sequence Gln-Tyr-Asp-Gly-Lys-Gly-Val-Gly (SEQ. ID NO: 3) or consists essentially of the sequence Gln-Tyr-Asp-Gly-Lys-Gly-Val-Gly (SEQ. ID NO: 3) modified by the addition or omission of one or more amino acids while retaining the ability to raise antibodies recognising a corresponding native collagen fragment or to inhibit the binding of such antibodies to a corresponding native collagen fragment.

9. The kit of claim 6, wherein said immunological binding partner is a whole antibody.

10. The kit of claim 9, wherein said antibody is a monoclonal antibody.

11. A method of assaying collagen fragments in a body fluid which comprises contacting an immunological binding partner with the body fluid and a synthetic peptide, wherein the immunological binding partner is immunoreactive with the immobilized synthetic peptide and with an immobilized peptide consisting essentially of the amino acid sequence Gln-Tyr-Asp-Gly-Lys-Gly-Val-Gly (SEQ. ID NO: 3), and wherein the synthetic peptide contains no collagen cross-link structures and is immobilized on a solid surface.

* * * * *

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
      (A) LENGTH: 7 amino acids
      (B) TYPE: amino acid
      (D) TOPOLOGY: linear (ii) MOLECULE TYPE: peptide (v) FRAGMENT TYPE: N-terminal (vi) ORIGINAL SOURCE:
      (A) ORGANISM: Homo sap iens (vii) IMMEDIATE SOURCE:
      (B) CLONE: COLLAGEN TY PE I-alpha 1 -N term (xi) SEQUENCE DESCRIPTION: SEQ ID NO:1:

Asp Glu Lys Ser Thr Gly Gly
1              5

(2) INFORMATION FOR SEQ ID NO:2:

(i) SEQUENCE CHARACTERISTICS:
      (A) LENGTH: 8 amino acids
      (B) TYPE: amino acid
      (D) TOPOLOGY: linear (ii) MOLECULE TYPE: peptide (v) FRAGMENT TYPE: C-terminal (vi) ORIGINAL SOURCE:
      (A) ORGANISM: Homo sap iens (vii) IMMEDIATE SOURCE:
      (B) CLONE: COLLAGEN TY PE I -ALPHA 1- c TERMINAL (xi) SEQUENCE DESCRIPTION: SEQ ID NO:2:

```
Glu Lys Ala His Asp Gly Gly Arg
1               5
```

(2) INFORMATION FOR SEQ ID NO:3:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (v) FRAGMENT TYPE: N-terminal (vi) ORIGINAL SOURCE:
        (A) ORGANISM: Homo sap iens (vii) IMMEDIATE SOURCE:
        (B) CLONE: COLLAGEN TY PE I - ALPHA 2- N TERMINAL (xi) SEQUENCE DESCRIPTION: SEQ ID NO:3:

```
Gln Tyr Asp Gly Lys Gly Val Gly
1               5
```

(2) INFORMATION FOR SEQ ID NO:4:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (vi) ORIGINAL SOURCE:
        (A) ORGANISM: Homo sap iens (vii) IMMEDIATE SOURCE:
        (B) CLONE: COLLAGEN TY PE I -ALPHA 1- NEAR N (xi) SEQUENCE DESCRIPTION: SEQ ID NO:4:

```
Gly Met Lys Gly His Arg
1               5
```

(2) INFORMATION FOR SEQ ID NO:5:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: C-terminal (vi) ORIGINAL SOURCE:
        (A) ORGANISM: Homo sap iens (vii) IMMEDIATE SOURCE:
        (B) CLONE: COLLAGEN TY PE I -ALPHA 1 NEAR c (xi) SEQUENCE DESCRIPTION: SEQ ID NO:5:

```
Gly Ile Lys Gly His Arg
1               5
```

(2) INFORMATION FOR SEQ ID NO:6:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (vi) ORIGINAL SOURCE:
             (A) ORGANISM: Homo sap iens (vii) IMMEDIATE SOURCE:
             (B) CLONE: COLLAGEN TY PE I- ALPHA 2- NEAR N (xi) SEQUENCE DESCRIPTION: SEQ ID NO:6:

Gly Phe Lys Gly Ile Arg
1               5

(2) INFORMATION FOR SEQ ID NO:7:

(i) SEQUENCE CHARACTERISTICS:
             (A) LENGTH: 9 amino acids
             (B) TYPE: amino acid
             (D) TOPOLOGY: linear (ii) MOLECULE TYPE: peptide (v) FRAGMENT TYPE: internal (vi) ORIGINAL SOURCE:
             (A) ORGANISM: Homo sap iens (vii) IMMEDIATE SOURCE:
             (B) CLONE: COLLAGEN TY PE I - ALPHA 2 - NEAR C (xi) SEQUENCE DESCRIPTION: SEQ ID NO:7:

Gly Leu Pro Gly Leu Lys Gly His Asn
1               5

(2) INFORMATION FOR SEQ ID NO:8:

(i) SEQUENCE CHARACTERISTICS:
             (A) LENGTH: 6 amino acids
             (B) TYPE: amino acid
             (D) TOPOLOGY: linear (ii) MOLECULE TYPE: peptide (v) FRAGMENT TYPE: N-terminal (vi) ORIGINAL SOURCE:
             (A) ORGANISM: Homo sap iens (vii) IMMEDIATE SOURCE:
             (B) CLONE: COLLAGEN TY PE II- ALPHA 1- N TERM (xi) SEQUENCE DESCRIPTION: SEQ ID NO:8:

Pro Gly Pro Lys Gly Glu
1               5

(2) INFORMATION FOR SEQ ID NO:9:

(i) SEQUENCE CHARACTERISTICS:
             (A) LENGTH: 6 amino acids
             (B) TYPE: amino acid
             (D) TOPOLOGY: linear (ii) MOLECULE TYPE: peptide (v) FRAGMENT TYPE: N-terminal (vi) ORIGINAL SOURCE:
             (A) ORGANISM: Homo sap iens (vii) IMMEDIATE SOURCE:
             (B) CLONE: COLLAGEN TY PE II- ALPHA 1 N2

(xi) SEQUENCE DESCRIPTION: SEQ ID NO:9:

Gly Gln Lys Gly Glu Pro
1               5

(2) INFORMATION FOR SEQ ID NO:10:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (v) FRAGMENT TYPE: N-terminal (vi) ORIGINAL SOURCE:
            (A) ORGANISM: Homo sap iens (vii) IMMEDIATE SOURCE:
            (B) CLONE: COLLAGEN TY PE II - ALPHA 1- N3

(xi) SEQUENCE DESCRIPTION: SEQ ID NO:10:

Gly Asp Ile Lys Asp Ile Val
1               5

(2) INFORMATION FOR SEQ ID NO:11:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (v) FRAGMENT TYPE: C-terminal (vi) ORIGINAL SOURCE:
            (A) ORGANISM: Homo sap iens (vii) IMMEDIATE SOURCE:
            (B) CLONE: COLLAGEN TY PE II - ALPHA 1 -C TERM (xi) SEQUENCE DESCRIPTION: SEQ ID NO:11:

Glu Lys Gly Pro Asp
1               5

(2) INFORMATION FOR SEQ ID NO:12:

(i) SEQUENCE CHARACTERISTICS:
            (A) LENGTH: 3 amino acids
            (B) TYPE: amino acid
            (D) TOPOLOGY: linear (ii) MOLECULE TYPE: peptide (v) FRAGMENT TYPE: internal (vi) ORIGINAL SOURCE:
            (A) ORGANISM: Homo sap iens (vii) IMMEDIATE SOURCE:
            (B) CLONE: COLLAGEN TY PE II - ALPHA 1 - NEAR N (xi) SEQUENCE DESCRIPTION: SEQ ID NO:12:

Gly Val Lys
1

(2) INFORMATION FOR SEQ ID NO:13:

(i) SEQUENCE CHARACTERISTICS:

(A) LENGTH: 5 amino acids
            (B) TYPE: amino acid
            (D) TOPOLOGY: linear (ii) MOLECULE TYPE: peptide (v) FRAGMENT TYPE: internal (vi) ORIGINAL SOURCE:
            (A) ORGANISM: Homo sap iens (vii) IMMEDIATE SOURCE:
            (B) CLONE: COLLAGEN TY PE II - ALPHA 1 -NEAR N2

(xi) SEQUENCE DESCRIPTION: SEQ ID NO:13:

Pro Gly Val Lys Gly
1               5

(2) INFORMATION FOR SEQ ID NO:14:

(i) SEQUENCE CHARACTERISTICS:
            (A) LENGTH: 6 amino acids
            (B) TYPE: amino acid
            (D) TOPOLOGY: linear (ii) MOLECULE TYPE: peptide (v) FRAGMENT TYPE: N-terminal (vi) ORIGINAL SOURCE:
            (A) ORGANISM: Homo sap iens (vii) IMMEDIATE SOURCE:
            (B) CLONE: COLLAGEN TY PE III -ALPHA 1 - N TERM (xi) SEQUENCE DESCRIPTION: SEQ ID NO:14:

Asp Val Lys Ser Gly Val
1               5

(2) INFORMATION FOR SEQ ID NO:15:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (v) FRAGMENT TYPE: C-terminal (vi) ORIGINAL SOURCE:
            (A) ORGANISM: Homo sap iens (vii) IMMEDIATE SOURCE:
            (B) CLONE: COLLAGEN TY PE III - ALPHA 1 - C TERM (xi) SEQUENCE DESCRIPTION: SEQ ID NO:15:

Glu Lys Ala Gly Gly Phe Ala
1               5

(2) INFORMATION FOR SEQ ID NO:16:

(i) SEQUENCE CHARACTERISTICS:
            (A) LENGTH: 9 amino acids
            (B) TYPE: amino acid
            (D) TOPOLOGY: linear (ii) MOLECULE TYPE: peptide (v) FRAGMENT TYPE: internal (vi) ORIGINAL SOURCE:
            (A) ORGANISM: Homo sap iens (vii) IMMEDIATE SOURCE:
          (B) CLONE: COLLAGEN TY PE III - ALPHA 1 - NEAR N (xi) SEQUENCE DESCRIPTION: SEQ ID NO:16:

Gly Phe Pro Gly Met Lys Gly His Arg
1               5

(2) INFORMATION FOR SEQ ID NO:17:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (vi) ORIGINAL SOURCE:
         (A) ORGANISM: Homo sap iens (vii) IMMEDIATE SOURCE:
          (B) CLONE: COLLAGEN TY PE III - ALPHA 1 - NEAR C (xi) SEQUENCE DESCRIPTION: SEQ ID NO:17:

Gly Ala Ala Gly Ile Lys Gly His Arg
1               5

(2) INFORMATION FOR SEQ ID NO:18:

(i) SEQUENCE CHARACTERISTICS:
        (A) LENGTH: 1341 amino  acids
        (B) TYPE: amino acid
        (D) TOPOLOGY: linear (ii) MOLECULE TYPE: protein (vi) ORIGINAL SOURCE:
         (A) ORGANISM: Homo sap iens (vii) IMMEDIATE SOURCE:
          (B) CLONE: COLLAGEN AL PHA 1 (I)

(xi) SEQUENCE DESCRIPTION: SEQ ID NO:18:

Met Phe Ser Phe Val Asp Leu Arg Leu L eu Leu Leu Ala Ala Thr
1               5                   10                  15

Ala Leu Leu Thr His Gly Gln Glu Glu Gly G ln Val Glu Gly Gln Asp
                20              25                  30

Glu Asp Ile Pro Pro Ile Thr Cys Val Gln A sn Gly Leu Arg Tyr His
                35              40                  45

Asp Arg Asp Val Trp Lys Pro Glu Pro Cys G ln Ile Cys Val Cys Asp
    50                  55                  60

Asn Gly Lys Val Leu Cys Asp Asp Val Ile C ys Asp Glu Thr Lys Asn
65                  70                  75                  80

Cys Pro Gly Ala Glu Val Pro Glu Gly Glu C ys Cys Pro Val Cys Pro
                85                  90                  95

Asp Gly Ser Glu Ser Pro Thr Asp Gln Glu T hr Thr Gly Val Glu Gly
                100             105                 110

Pro Lys Gly Asp Thr Gly Pro Arg Gly Pro A rg Gly Pro Ala Gly Pro
                115             120                 125

Pro Gly Arg Asp Gly Ile Pro Gly Gln Pro G ly Leu Pro Gly Pro Pro
                130             135                 140

Gly Pro Pro Gly Pro Pro Gly Pro Pro Gly L eu Gly Gly Asn Phe Ala
145                 150             155                 160

-continued

```
Pro Gln Leu Tyr Gly Tyr Asp Glu Lys Ser Thr Gly Gly Ile Ser Val
                165                 170                 175
Pro Gly Pro Met Gly Pro Ser Gly Pro Arg Gly Leu Pro Gly Pro Pro
                180                 185                 190
Gly Ala Pro Gly Pro Glx Gly Phe Glx Gly Pro Pro Gly Glx Pro Gly
                195                 200                 205
Glx Pro Gly Ala Ser Gly Pro Met Gly Pro Arg Gly Pro Pro Gly Pro
        210                 215                 220
Pro Gly Lys Asx Gly Asx Asx Gly Glx Ala Gly Lys Pro Gly Arg Pro
225                 230                 235                 240
Gly Glx Arg Gly Pro Pro Gly Glx Gly Ala Arg Gly Leu Pro Gly
                245                 250                 255
Thr Ala Gly Leu Pro Gly Met Lys Gly His Arg Gly Phe Ser Gly Leu
                260                 265                 270
Asx Gly Ala Lys Gly Asx Ala Gly Pro Ala Gly Pro Lys Gly Glx Pro
                275                 280                 285
Gly Ser Pro Gly Glx Asx Gly Ala Pro Gly Glx Met Gly Pro Pro Gly
        290                 295                 300
Pro Lys Gly Asn Ser Gly Glu Pro Gly Ala Pro Gly Ser Lys Gly Asp
305                 310                 315                 320
Thr Gly Ala Lys Gly Glu Pro Gly Pro Val Gly Val Gln Gly Pro Pro
                325                 330                 335
Gly Pro Ala Gly Glu Glu Gly Lys Arg Gly Ala Arg Gly Glu Pro Gly
                340                 345                 350
Pro Thr Gly Leu Pro Gly Pro Gly Glu Arg Gly Pro Gly Ser
                355                 360                 365
Arg Gly Phe Pro Gly Ala Asp Gly Val Ala Gly Pro Lys Gly Pro Ala
        370                 375                 380
Gly Glu Arg Gly Ser Pro Gly Pro Ala Gly Pro Lys Gly Ser Pro Gly
385                 390                 395                 400
Glu Ala Gly Arg Pro Gly Glu Ala Gly Leu Pro Gly Ala Lys Gly Leu
                405                 410                 415
Thr Gly Ser Pro Gly Ser Pro Gly Pro Asp Gly Lys Thr Gly Pro Pro
                420                 425                 430
Gly Pro Ala Gly Gln Asp Gly Arg Pro Gly Pro Pro Gly Pro Pro Gly
        435                 440                 445
Ala Arg Gly Gln Ala Gly Val Met Gly Phe Pro Gly Pro Lys Gly Ala
        450                 455                 460
Ala Gly Glu Pro Gly Lys Ala Gly Glu Arg Gly Val Pro Gly Pro Pro
465                 470                 475                 480
Gly Ala Val Gly Pro Ala Gly Lys Asp Gly Glu Ala Gly Ala Gln Gly
                485                 490                 495
Pro Pro Gly Pro Ala Gly Pro Ala Gly Glu Arg Gly Glu Gln Gly Pro
                500                 505                 510
Ala Gly Ser Pro Gly Phe Gln Gly Leu Pro Gly Pro Ala Gly Pro Pro
                515                 520                 525
Gly Glu Ala Gly Lys Pro Gly Glu Gln Gly Val Pro Gly Asp Leu Gly
        530                 535                 540
Ala Pro Gly Pro Ser Gly Ala Arg Gly Glu Arg Gly Phe Pro Gly Glu
545                 550                 555                 560
Arg Gly Val Gln Gly Pro Pro Gly Pro Ala Gly Pro Arg Gly Ala Asn
                565                 570                 575
```

```
Gly Ala Pro Gly Asn Asp Gly Ala Lys Gly Asp Ala Gly Ala Pro Gly
            580                 585                 590

Ala Pro Gly Ser Gln Gly Ala Pro Gly Leu Gln Gly Met Pro Gly Glu
        595                 600                 605

Arg Gly Ala Ala Gly Leu Pro Gly Pro Lys Gly Asp Arg Gly Asp Ala
    610                 615                 620

Gly Pro Lys Gly Ala Asp Gly Ser Pro Gly Lys Asp Gly Val Arg Gly
625                 630                 635                 640

Leu Thr Gly Pro Ile Gly Pro Pro Gly Pro Ala Gly Ala Pro Gly Asp
                645                 650                 655

Lys Gly Glu Ser Gly Pro Ser Gly Pro Ala Gly Pro Thr Gly Ala Arg
            660                 665                 670

Gly Ala Pro Gly Asp Arg Gly Glu Pro Gly Pro Pro Gly Pro Ala Gly
        675                 680                 685

Phe Ala Gly Pro Pro Gly Ala Asp Gly Gln Pro Gly Ala Lys Gly Glu
    690                 695                 700

Pro Gly Asp Ala Gly Ala Lys Gly Asp Ala Gly Pro Pro Gly Pro Ala
705                 710                 715                 720

Gly Pro Ala Gly Pro Pro Gly Pro Ile Gly Asn Val Gly Ala Pro Gly
                725                 730                 735

Ala Lys Gly Ala Arg Gly Ser Ala Gly Pro Pro Gly Ala Thr Gly Phe
            740                 745                 750

Pro Gly Ala Ala Gly Arg Val Gly Pro Pro Gly Pro Ser Gly Asn Ala
        755                 760                 765

Gly Pro Pro Gly Pro Pro Gly Pro Ala Gly Lys Glu Gly Gly Lys Gly
    770                 775                 780

Pro Arg Gly Glu Thr Gly Pro Ala Gly Arg Pro Gly Glu Val Gly Pro
785                 790                 795                 800

Pro Gly Pro Pro Gly Pro Ala Gly Glu Lys Gly Ser Pro Gly Ala Asp
                805                 810                 815

Gly Pro Ala Gly Ala Pro Gly Thr Pro Gly Pro Gln Gly Ile Ala Gly
            820                 825                 830

Gln Arg Gly Val Val Gly Leu Pro Gly Gln Arg Gly Glu Arg Gly Phe
        835                 840                 845

Pro Gly Leu Pro Gly Pro Ser Gly Glu Pro Gly Lys Gln Gly Pro Ser
    850                 855                 860

Gly Ala Ser Gly Glu Arg Gly Pro Pro Gly Pro Met Gly Pro Pro Gly
865                 870                 875                 880

Leu Ala Gly Pro Pro Gly Glu Ser Gly Arg Glu Gly Ala Pro Gly Ala
                885                 890                 895

Glu Gly Ser Pro Gly Arg Asp Gly Ser Pro Gly Ala Lys Gly Asp Arg
            900                 905                 910

Gly Glu Thr Gly Pro Ala Gly Pro Pro Gly Ala Xaa Gly Ala Xaa Gly
        915                 920                 925

Ala Pro Gly Pro Val Gly Pro Ala Gly Lys Ser Gly Asp Arg Gly Glu
    930                 935                 940

Thr Gly Pro Ala Gly Pro Ala Gly Pro Val Gly Pro Ala Gly Ala Arg
945                 950                 955                 960

Gly Pro Ala Gly Pro Gln Gly Pro Arg Gly Asp Lys Gly Glu Thr Gly
                965                 970                 975

Glu Gln Gly Asp Arg Gly Ile Lys Gly His Arg Gly Phe Ser Gly Leu
            980                 985                 990

Gln Gly Pro Pro Gly Pro Pro Gly Ser Pro Gly Glu Gln Gly Pro Ser
```

```
                995                1000                    1005
Gly Ala Ser Gly Pro Ala Gly Pro Arg Gly Pro Pro Gly Ser Ala Gly
        1010                1015                1020
Ala Pro Gly Lys Asp Gly Leu Asn Gly Leu Pro Gly Pro Ile Gly Pro
1025                103 0                1035                1040
Pro Gly Pro Arg Gly Arg Thr Gly Asp Ala Gly Pro Val Gly Pro Pro
                1045                1050                1055
Gly Pro Pro Gly Pro Pro Gly Pro Pro Gly Pro Pro Ser Ala Gly Phe
            1060                1065                1070
Asp Phe Ser Phe Leu Pro Gln Pro Pro Gln Glu Lys Ala His Lys Gly
        1075                1080                1085
Gly Arg Tyr Tyr Arg Ala Asp Asp Ala Asn Val Val Arg Asp Arg Asp
    1090                1095                1100
Leu Glu Val Asp Thr Thr Leu Lys Ser Leu Ser Gln Gln Ile Glu Asn
1105                111 0                1115                1120
Ile Arg Ser Pro Glu Gly Xaa Arg Lys Asn Pro Ala Arg Thr Cys Arg
                1125                1130                1135
Asp Leu Lys Met Cys His Ser Asp Trp Lys Ser Gly Glu Tyr Trp Ile
            1140                1145                1150
Asp Pro Asn Gln Gly Cys Asn Leu Asp Ala Ile Lys Val Phe Cys Asn
        1155                1160                1165
Met Glu Thr Gly Glu Thr Cys Val Tyr Pro Thr Gln Pro Ser Val Ala
    1170                1175                1180
Gln Lys Asn Trp Tyr Ile Ser Lys Asn Pro Lys Asp Lys Asp Arg His
1185                119 0                1195                1200
Val Trp Phe Gly Glu Ser Met Thr Asp Gly Phe Gln Phe Glu Tyr Gly
                1205                1210                1215
Gly Gln Gly Ser Asp Pro Ala Asp Val Ala Ile Gln Leu Thr Phe Leu
            1220                1225                1230
Arg Leu Met Ser Thr Glu Ala Ser Gln Asn Ile Thr Tyr His Cys Lys
        1235                1240                1245
Asn Ser Val Ala Tyr Met Asp Gln Gln Thr Gly Asn Leu Lys Lys Ala
    1250                1255                1260
Leu Leu Leu Xaa Gly Ser Asn Glu Ile Glu Ile Arg Ala Glu Gly Asn
1265                127 0                1275                1280
Ser Arg Phe Thr Tyr Ser Val Thr Val Asp Gly Cys Thr Ser His Thr
                1285                1290                1295
Gly Ala Trp Gly Lys Thr Val Ile Glu Tyr Lys Thr Thr Lys Ser Ser
            1300                1305                1310
Arg Leu Pro Ile Ile Asp Val Ala Pro Leu Asp Val Gly Ala Pro Asp
        1315                1320                1325
Gln Glu Phe Gly Phe Asp Val Gly Pro Val Cys Phe Leu
    1330                1335                1340

(2) INFORMATION FOR SEQ ID NO:19:

(i) SEQUENCE CHARACTERISTICS:
        (A) LENGTH: 1366 amino acids
        (B) TYPE: amino acid
        (D) TOPOLOGY: linear (ii) MOLECULE TYPE: protein (vi) ORIGINAL SOURCE:
        (A) ORGANISM: Homo sap iens (vii) IMMEDIATE SOURCE:
```

(B) CLONE: collagen alpha 2- type I (xi) SEQUENCE DESCRIPTION: SEQ ID NO:19:

```
Met Leu Ser Phe Val Asp Thr Arg Thr Leu Leu Leu Leu Ala Val Thr
1               5                   10                  15

Leu Cys Leu Ala Thr Cys Gln Ser Leu Gln Glu Glu Thr Val Arg Lys
            20                  25                  30

Gly Pro Ala Gly Asp Arg Gly Pro Arg Gly Glu Arg Gly Pro Pro Gly
            35                  40                  45

Pro Pro Gly Arg Asp Gly Glu Asp Gly Pro Thr Gly Pro Pro Gly Pro
        50                  55                  60

Pro Gly Pro Pro Gly Pro Pro Gly Leu Gly Gly Asn Phe Ala Ala Gln
65                  70                  75                  80

Tyr Asp Gly Lys Gly Val Gly Leu Gly Pro Gly Pro Met Gly Leu Met
                85                  90                  95

Gly Pro Arg Gly Pro Pro Gly Ala Ala Gly Ala Pro Gly Pro Gln Gly
            100                 105                 110

Phe Gln Gly Pro Ala Gly Glu Pro Gly Glu Pro Gly Gln Thr Gly Pro
            115                 120                 125

Ala Gly Ala Arg Gly Pro Ala Gly Pro Pro Gly Lys Ala Gly Glu Asp
        130                 135                 140

Gly His Pro Gly Lys Pro Gly Arg Pro Gly Glu Arg Gly Val Val Gly
145                 150                 155                 160

Pro Gln Gly Ala Arg Gly Phe Pro Gly Thr Pro Gly Leu Pro Gly Phe
                165                 170                 175

Lys Gly Ile Arg Gly His Asn Gly Leu Asp Gly Leu Lys Gly Gln Pro
            180                 185                 190

Gly Ala Pro Gly Val Lys Gly Glu Pro Gly Ala Pro Gly Glu Asn Gly
            195                 200                 205

Thr Pro Gly Gln Thr Gly Ala Arg Gly Leu Pro Gly Glu Arg Gly Arg
        210                 215                 220

Val Gly Ala Pro Gly Pro Ala Gly Ala Arg Gly Ser Asp Gly Ser Val
225                 230                 235                 240

Gly Pro Val Gly Pro Ala Gly Pro Asn Gly Ser Ala Gly Pro Pro Gly
                245                 250                 255

Phe Pro Gly Ala Pro Gly Pro Lys Gly Glu Ile Gly Ala Val Gly Asn
            260                 265                 270

Ala Gly Pro Thr Gly Pro Ala Gly Pro Arg Gly Glu Val Gly Leu Pro
            275                 280                 285

Gly Leu Ser Gly Pro Val Gly Pro Pro Gly Asn Pro Gly Ala Asn Gly
        290                 295                 300

Leu Thr Gly Ala Lys Gly Ala Ala Gly Leu Pro Gly Val Ala Gly Ala
305                 310                 315                 320

Pro Gly Leu Pro Gly Pro Arg Gly Ile Pro Gly Pro Pro Gly Ala Ala
                325                 330                 335

Gly Thr Thr Gly Ala Arg Gly Leu Val Gly Glu Pro Gly Pro Ala Gly
            340                 345                 350

Ser Lys Gly Glu Ser Gly Asn Lys Gly Glu Pro Gly Ser Ala Gly Pro
            355                 360                 365

Gln Gly Pro Pro Gly Pro Ser Gly Glu Glu Gly Lys Arg Gly Pro Asn
        370                 375                 380

Gly Glu Ala Gly Ser Ala Gly Pro Pro Gly Pro Pro Gly Leu Arg Gly
385                 390                 395                 400
```

```
Ser Pro Gly Ser Arg Gly Leu Pro Gly Asp Gly Arg Ala Gly Val
            405                 410                 415

Met Gly Pro Pro Gly Ser Arg Gly Ala Ser Gly Pro Ala Gly Val Arg
            420                 425                 430

Gly Pro Asn Gly Asp Ala Gly Arg Pro Gly Glu Pro Gly Leu Met Gly
            435                 440                 445

Pro Arg Gly Leu Pro Gly Ser Pro Gly Asn Ile Gly Pro Ala Gly Lys
450                 455                 460

Glu Gly Pro Val Gly Leu Pro Gly Ile Asp Gly Arg Pro Gly Pro Ile
465                 470                 475                 480

Gly Pro Val Gly Ala Arg Gly Glu Pro Gly Asn Ile Gly Phe Pro Gly
            485                 490                 495

Pro Lys Gly Pro Thr Gly Asp Pro Gly Lys Asn Gly Asp Lys Gly His
            500                 505                 510

Ala Gly Leu Ala Gly Ala Arg Gly Ala Pro Gly Pro Asp Gly Asn Asn
            515                 520                 525

Gly Ala Gln Gly Pro Pro Gly Pro Gln Gly Val Gln Gly Gly Lys Gly
            530                 535                 540

Glu Gln Gly Pro Ala Gly Pro Pro Gly Phe Gln Gly Leu Pro Gly Pro
545                 550                 555                 560

Ser Gly Pro Ala Gly Glu Val Gly Lys Pro Gly Glu Arg Gly Leu His
            565                 570                 575

Gly Glu Phe Gly Leu Pro Gly Pro Ala Gly Pro Arg Gly Glu Arg Gly
            580                 585                 590

Pro Pro Gly Glu Ser Gly Ala Ala Gly Pro Thr Gly Pro Ile Gly Ser
            595                 600                 605

Arg Gly Pro Ser Gly Pro Pro Gly Pro Asp Gly Asn Lys Gly Glu Pro
            610                 615                 620

Gly Val Val Gly Ala Val Gly Thr Ala Gly Pro Ser Gly Pro Ser Gly
625                 630                 635                 640

Leu Pro Gly Glu Arg Gly Ala Ala Gly Ile Pro Gly Gly Lys Gly Glu
            645                 650                 655

Lys Gly Glu Pro Gly Leu Arg Gly Glu Ile Gly Asn Pro Gly Arg Asp
            660                 665                 670

Gly Ala Arg Gly Ala His Gly Ala Val Gly Ala Pro Gly Pro Ala Gly
            675                 680                 685

Ala Thr Gly Asp Arg Gly Glu Ala Gly Ala Ala Gly Pro Ala Gly Pro
690                 695                 700

Ala Gly Pro Arg Gly Ser Pro Gly Glu Arg Gly Glu Val Gly Pro Ala
705                 710                 715                 720

Gly Pro Asn Gly Phe Ala Gly Pro Ala Gly Ala Ala Gly Gln Pro Gly
            725                 730                 735

Ala Lys Gly Glu Arg Gly Gly Lys Gly Pro Lys Gly Glu Asn Gly Val
            740                 745                 750

Val Gly Pro Thr Gly Pro Val Gly Ala Ala Gly Pro Ala Gly Pro Asn
            755                 760                 765

Gly Pro Pro Gly Pro Ala Gly Ser Arg Gly Asp Gly Gly Pro Pro Gly
            770                 775                 780

Met Thr Gly Phe Pro Gly Ala Ala Gly Arg Thr Gly Pro Pro Gly Pro
785                 790                 795                 800

Ser Gly Ile Ser Gly Pro Pro Gly Pro Pro Gly Pro Ala Gly Lys Glu
            805                 810                 815

Gly Leu Arg Gly Pro Arg Gly Asp Gln Gly Pro Val Gly Arg Thr Gly
```

-continued

```
                820                 825                 830
Glu Val Gly Ala Val Gly Pro Pro Gly Phe Ala Gly Glu Lys Gly Pro
                835                 840                 845
Ser Gly Glu Ala Gly Thr Ala Gly Pro Gly Thr Pro Gly Pro Gln
850                 855                 860
Gly Leu Leu Gly Ala Pro Gly Ile Leu Gly Leu Pro Gly Ser Arg Gly
865                 870                 875                 880
Glu Arg Gly Leu Pro Gly Val Ala Gly Val Gly Glu Pro Gly Pro
                885                 890                 895
Leu Gly Ile Ala Gly Pro Gly Ala Arg Gly Pro Pro Gly Ala Val
                900                 905                 910
Gly Ser Pro Gly Val Asn Gly Ala Pro Gly Glu Ala Gly Arg Asp Gly
                915                 920                 925
Asn Pro Gly Asn Asp Gly Pro Pro Gly Arg Asp Gly Gln Pro Gly His
930                 935                 940
Lys Gly Glu Arg Gly Tyr Pro Gly Asn Ile Gly Pro Val Gly Ala Ala
945                 950                 955                 960
Gly Ala Pro Gly Pro His Gly Pro Val Gly Pro Ala Gly Lys His Gly
                965                 970                 975
Asn Arg Gly Glu Thr Gly Pro Ser Gly Pro Val Gly Pro Ala Gly Ala
                980                 985                 990
Val Gly Pro Arg Gly Pro Ser Gly Pro Gln Gly Ile Arg Gly Asp Lys
                995                 1000                1005
Gly Glu Pro Gly Glu Lys Gly Pro Arg Gly Leu Pro Gly Phe Lys Gly
                1010                1015                1020
His Asn Gly Leu Gln Gly Leu Pro Gly Ile Ala Gly His His Gly Asp
1025                1030                1035                1040
Gln Gly Ala Pro Gly Ser Val Gly Pro Ala Gly Pro Arg Gly Pro Ala
                1045                1050                1055
Gly Pro Ser Gly Pro Ala Gly Lys Asp Gly Arg Thr Gly His Pro Gly
                1060                1065                1070
Thr Val Gly Pro Ala Gly Ile Arg Gly Pro Gln Gly His Gln Gly Pro
                1075                1080                1085
Ala Gly Pro Pro Gly Pro Pro Gly Pro Pro Gly Pro Pro Gly Val Ser
                1090                1095                1100
Gly Gly Gly Tyr Asp Phe Gly Tyr Asp Gly Asp Phe Tyr Arg Ala Asp
1105                1110                1115                1120
Gln Pro Arg Ser Ala Pro Ser Leu Arg Pro Lys Asp Tyr Glu Val Asp
                1125                1130                1135
Ala Thr Leu Lys Ser Leu Asn Asn Gln Ile Glu Thr Leu Leu Thr Pro
                1140                1145                1150
Glu Gly Ser Arg Lys Asn Pro Ala Arg Thr Cys Arg Asp Leu Arg Leu
                1155                1160                1165
Ser His Pro Glu Trp Ser Ser Gly Tyr Tyr Trp Ile Asp Pro Asn Gln
                1170                1175                1180
Gly Cys Thr Met Glu Ala Ile Lys Val Tyr Cys Asp Phe Pro Thr Gly
1185                1190                1195                1200
Glu Thr Cys Ile Arg Ala Gln Pro Glu Asn Ile Pro Ala Lys Asn Trp
                1205                1210                1215
Tyr Arg Ser Ser Lys Asp Lys Lys His Val Trp Leu Gly Glu Thr Ile
                1220                1225                1230
Asn Ala Gly Ser Gln Phe Glu Tyr Asn Val Glu Gly Val Thr Ser Lys
                1235                1240                1245
```

-continued

```
Glu Met Ala Thr Gln Leu Ala Phe Met Arg Leu Leu Ala Asn Tyr Ala
    1250                1255                1260

Ser Gln Asn Ile Thr Tyr His Cys Lys Asn Ser Ile Ala Tyr Met Asp
1265                1270                1275                1280

Glu Glu Thr Gly Asn Leu Lys Lys Ala Val Ile Leu Gln Gly Ser Asn
                1285                1290                1295

Asp Val Glu Leu Val Ala Glu Gly Asn Ser Arg Phe Thr Tyr Thr Val
                1300                1305                1310

Leu Val Asp Gly Cys Ser Lys Lys Thr Asn Glu Trp Gly Lys Thr Ile
            1315                1320                1325

Ile Glu Tyr Lys Thr Asn Lys Pro Ser Arg Leu Pro Phe Leu Asp Ile
        1330                1335                1340

Ala Pro Leu Asp Ile Gly Gly Ala Asp His Glu Phe Phe Val Asp Ile
1345                1350                1355                1360

Gly Pro Val Cys Phe Lys
            1365
```

(2) INFORMATION FOR SEQ ID NO:20:

(i) SEQUENCE CHARACTERISTICS:
        (A) LENGTH: 1418 amino acids
        (B) TYPE: amino acid
        (D) TOPOLOGY: linear (ii) MOLECULE TYPE: protein (vi) ORIGINAL SOURCE:
        (A) ORGANISM: Homo sapiens (vii) IMMEDIATE SOURCE:
        (B) CLONE: COLLAGEN -ALPHA 1 (II)

(xi) SEQUENCE DESCRIPTION: SEQ ID NO:20:

```
Met Ile Arg Leu Gly Ala Pro Gln Ser Leu Val Leu Leu Thr Leu Leu
1               5                   10                  15

Val Ala Ala Val Leu Arg Cys Gln Gly Gln Asp Val Arg Gln Pro Gly
            20                  25                  30

Pro Lys Gly Gln Lys Gly Glu Pro Gly Asp Ile Lys Asp Ile Val Gly
        35                  40                  45

Pro Lys Gly Pro Pro Gly Pro Gln Gly Pro Ala Gly Glu Gln Gly Pro
    50                  55                  60

Arg Gly Asp Arg Gly Asp Lys Gly Glu Lys Gly Ala Pro Gly Pro Arg
65                  70                  75                  80

Gly Arg Asp Gly Glu Pro Gly Thr Leu Gly Asn Pro Gly Pro Pro Gly
                85                  90                  95

Pro Pro Gly Pro Pro Gly Pro Pro Gly Leu Gly Gly Asn Phe Ala Ala
                100                 105                 110

Gln Met Ala Gly Gly Phe Asp Glu Lys Ala Gly Gly Ala Gln Leu Gly
            115                 120                 125

Val Met Gln Gly Pro Met Gly Pro Met Gly Pro Arg Gly Pro Pro Gly
        130                 135                 140

Pro Ala Gly Ala Pro Gly Pro Gln Gly Phe Gln Gly Asn Pro Gly Glu
145                 150                 155                 160

Pro Gly Glu Pro Gly Val Ser Gly Pro Met Gly Pro Arg Gly Pro Pro
                165                 170                 175

Gly Pro Pro Gly Lys Pro Gly Asp Asp Gly Glu Ala Gly Lys Pro Gly
                180                 185                 190
```

-continued

```
Lys Ala Gly Glu Arg Gly Pro Pro Gly Pro Gln Gly Ala Arg Gly Phe
    195                 200                 205

Pro Gly Thr Pro Gly Leu Pro Gly Val Lys Gly His Arg Gly Tyr Pro
    210                 215                 220

Gly Leu Asp Gly Ala Lys Gly Glu Ala Gly Ala Pro Gly Val Lys Gly
225                 230                 235                 240

Glu Ser Gly Ser Pro Gly Glu Asn Gly Ser Pro Gly Pro Met Gly Pro
                245                 250                 255

Arg Gly Leu Pro Gly Glu Arg Gly Arg Thr Gly Pro Ala Gly Ala Ala
            260                 265                 270

Gly Ala Arg Gly Asn Asp Gly Gln Pro Gly Pro Ala Gly Pro Pro Gly
        275                 280                 285

Pro Val Gly Pro Ala Gly Gly Pro Gly Phe Pro Gly Ala Pro Gly Ala
    290                 295                 300

Lys Gly Glu Ala Gly Pro Thr Gly Ala Arg Gly Pro Glu Gly Ala Gln
305                 310                 315                 320

Gly Pro Arg Gly Glu Pro Gly Thr Pro Gly Ser Pro Gly Pro Ala Gly
                325                 330                 335

Ala Ser Gly Asn Pro Gly Thr Asp Gly Ile Pro Gly Ala Lys Gly Ser
            340                 345                 350

Ala Gly Ala Pro Gly Ile Ala Gly Ala Pro Gly Phe Pro Gly Pro Arg
        355                 360                 365

Gly Pro Pro Asp Pro Gln Gly Ala Thr Gly Pro Leu Gly Pro Lys Gly
    370                 375                 380

Gln Thr Gly Lys Pro Gly Ile Ala Gly Phe Lys Gly Glu Gln Gly Pro
385                 390                 395                 400

Lys Gly Glu Pro Gly Pro Ala Gly Pro Gln Gly Ala Pro Gly Pro Ala
                405                 410                 415

Gly Glu Glu Gly Lys Arg Gly Ala Arg Gly Glu Pro Gly Gly Val Gly
            420                 425                 430

Pro Ile Gly Pro Pro Gly Glu Arg Gly Ala Pro Gly Asn Arg Gly Phe
        435                 440                 445

Pro Gly Gln Asp Gly Leu Ala Gly Pro Lys Gly Ala Pro Gly Glu Arg
    450                 455                 460

Gly Pro Ser Gly Leu Ala Gly Pro Lys Gly Ala Asn Gly Asp Pro Gly
465                 470                 475                 480

Arg Pro Gly Glu Pro Gly Leu Pro Gly Ala Arg Gly Leu Thr Gly Arg
                485                 490                 495

Pro Gly Asp Ala Gly Pro Gln Gly Lys Val Gly Pro Ser Gly Ala Pro
            500                 505                 510

Gly Glu Asp Gly Arg Pro Gly Pro Pro Gly Pro Gln Gly Ala Arg Gly
        515                 520                 525

Gln Pro Gly Val Met Gly Phe Pro Gly Pro Lys Gly Ala Asn Gly Glu
    530                 535                 540

Pro Gly Lys Ala Gly Glu Lys Gly Leu Pro Gly Ala Pro Gly Leu Arg
545                 550                 555                 560

Gly Leu Pro Gly Lys Asp Gly Glu Thr Gly Ala Glu Gly Pro Pro Gly
                565                 570                 575

Pro Ala Gly Pro Ala Gly Glu Arg Gly Glu Gln Gly Ala Pro Gly Pro
            580                 585                 590

Ser Gly Phe Gln Gly Leu Pro Gly Pro Pro Gly Pro Pro Gly Glu Gly
        595                 600                 605

Gly Lys Pro Gly Asp Gln Gly Val Pro Gly Glu Ala Gly Ala Pro Gly
```

-continued

```
            610                 615                 620
Leu Val Gly Pro Arg Gly Glu Arg Gly Phe Pro Gly Glu Arg Gly Ser
625                 630                 635                 640
Pro Gly Ala Gln Gly Leu Gln Gly Pro Arg Gly Leu Pro Gly Thr Pro
                    645                 650                 655
Gly Thr Asp Gly Pro Lys Gly Ala Ser Gly Pro Ala Gly Pro Pro Gly
            660                 665                 670
Ala Gln Gly Pro Pro Gly Leu Gln Gly Met Pro Gly Glu Arg Gly Ala
            675                 680                 685
Ala Gly Ile Ala Gly Pro Lys Gly Asp Arg Gly Asp Val Gly Glu Lys
690                 695                 700
Gly Pro Glu Gly Ala Pro Gly Lys Asp Gly Gly Arg Gly Leu Thr Gly
705                 710                 715                 720
Pro Ile Gly Pro Pro Gly Pro Ala Gly Ala Asn Gly Glu Lys Gly Glu
                    725                 730                 735
Val Gly Pro Pro Gly Pro Ala Gly Ser Ala Gly Ala Arg Gly Ala Pro
                    740                 745                 750
Gly Glu Arg Gly Glu Thr Gly Pro Pro Gly Thr Ser Gly Ile Ala Gly
            755                 760                 765
Pro Pro Gly Ala Asp Gly Gln Pro Gly Ala Lys Gly Glu Gln Gly Glu
770                 775                 780
Ala Gly Gln Lys Gly Asp Ala Gly Ala Pro Gly Pro Gln Gly Pro Ser
785                 790                 795                 800
Gly Ala Pro Gly Pro Gln Gly Pro Thr Gly Val Thr Gly Pro Lys Gly
                    805                 810                 815
Ala Arg Gly Ala Gln Gly Pro Pro Gly Ala Thr Gly Phe Pro Gly Ala
            820                 825                 830
Ala Gly Arg Val Gly Pro Pro Gly Ser Asn Gly Asn Pro Gly Pro Pro
            835                 840                 845
Gly Pro Pro Gly Pro Ser Gly Lys Asp Gly Pro Lys Gly Ala Arg Gly
850                 855                 860
Asp Ser Gly Pro Pro Gly Arg Ala Gly Glu Pro Gly Leu Gln Gly Pro
865                 870                 875                 880
Ala Gly Pro Pro Gly Glu Lys Gly Glu Pro Gly Asp Asp Gly Pro Ser
                    885                 890                 895
Gly Ala Glu Gly Pro Pro Gly Pro Gln Gly Leu Ala Gly Gln Arg Gly
            900                 905                 910
Ile Val Gly Leu Pro Gly Gln Arg Gly Glu Arg Gly Phe Pro Gly Leu
            915                 920                 925
Pro Gly Pro Ser Gly Glu Pro Gly Gln Gln Gly Ala Pro Gly Ala Ser
            930                 935                 940
Gly Asp Arg Gly Pro Pro Gly Pro Val Gly Pro Pro Gly Leu Thr Gly
945                 950                 955                 960
Pro Ala Gly Glu Pro Gly Arg Glu Gly Ser Pro Gly Ala Asp Gly Pro
                    965                 970                 975
Pro Gly Arg Asp Gly Ala Ala Gly Val Lys Gly Asp Arg Gly Glu Thr
            980                 985                 990
Gly Ala Val Gly Ala Pro Gly Ala Pro Gly Pro Pro Gly Ser Pro Gly
            995                 1000                1005
Pro Ala Gly Pro Thr Gly Lys Gln Gly Asp Arg Gly Glu Ala Gly Ala
            1010                1015                1020
Gln Gly Pro Met Gly Pro Ser Gly Pro Ala Gly Ala Arg Gly Ile Gln
1025                1030                1035                1040
```

Gly Pro Gln Gly Pro Arg Gly Asp Lys Gly Glu Ala Gly Glu Pro Gly
            1045                1050                1055

Glu Arg Gly Leu Lys Gly His Arg Gly Phe Thr Gly Leu Gln Gly Leu
        1060                1065                1070

Pro Gly Pro Pro Gly Pro Ser Gly Asp Gln Gly Ala Ser Gly Pro Ala
        1075                1080                1085

Gly Pro Ser Gly Pro Arg Gly Pro Pro Gly Pro Val Gly Pro Ser Gly
        1090                1095                1100

Lys Asp Gly Ala Asn Gly Ile Pro Gly Pro Ile Gly Pro Pro Gly Pro
1105                1110                1115                1120

Arg Gly Arg Ser Gly Glu Thr Gly Pro Ala Gly Pro Pro Gly Asn Pro
            1125                1130                1135

Gly Pro Pro Gly Pro Pro Gly Pro Pro Gly Pro Gly Ile Asp Met Ser
            1140                1145                1150

Ala Phe Ala Gly Leu Gly Pro Arg Glu Lys Gly Pro Asp Pro Leu Gln
            1155                1160                1165

Tyr Met Arg Ala Asp Gln Ala Ala Gly Gly Leu Arg Gln His Asp Ala
        1170                1175                1180

Glu Val Asp Ala Thr Leu Lys Ser Leu Asn Asn Gln Ile Glu Ser Ile
1185                1190                1195                1200

Arg Ser Pro Glu Gly Ser Arg Lys Asn Pro Ala Arg Thr Cys Arg Asp
            1205                1210                1215

Leu Lys Leu Cys His Pro Glu Trp Lys Ser Gly Asp Tyr Trp Ile Asp
            1220                1225                1230

Pro Asn Gln Gly Cys Thr Leu Asp Ala Met Lys Val Phe Cys Asn Met
        1235                1240                1245

Glu Thr Gly Glu Thr Cys Val Tyr Pro Asn Pro Ala Asn Val Pro Lys
        1250                1255                1260

Lys Asn Trp Trp Ser Ser Lys Ser Lys Glu Lys Lys His Ile Trp Phe
1265                1270                1275                1280

Gly Glu Thr Ile Asn Gly Gly Phe His Phe Ser Tyr Gly Asp Asp Asn
            1285                1290                1295

Leu Ala Pro Asn Thr Ala Asn Val Gln Met Thr Phe Leu Arg Leu Leu
        1300                1305                1310

Ser Thr Glu Gly Ser Gln Asn Ile Thr Tyr His Cys Lys Asn Ser Ile
        1315                1320                1325

Ala Tyr Leu Asp Glu Ala Ala Gly Asn Leu Lys Lys Ala Leu Leu Ile
        1330                1335                1340

Gln Gly Ser Asn Asp Val Glu Ile Arg Ala Glu Gly Asn Ser Arg Phe
1345                1350                1355                1360

Thr Tyr Thr Ala Leu Lys Asp Gly Cys Thr Lys His Thr Gly Lys Trp
            1365                1370                1375

Gly Lys Thr Val Ile Glu Tyr Arg Ser Gln Lys Thr Ser Arg Leu Pro
            1380                1385                1390

Ile Ile Asp Ile Ala Pro Met Asp Ile Gly Gly Pro Glu Gln Glu Phe
        1395                1400                1405

Gly Val Asp Ile Gly Pro Val Cys Phe Leu
    1410                1415

(2) INFORMATION FOR SEQ ID NO:21:

(i) SEQUENCE CHARACTERISTICS:
        (A) LENGTH: 1078 amino acids
        (B) TYPE: amino acid -continued

```
        (D) TOPOLOGY: linear (ii) MOLECULE TYPE: protein (vi) ORIGINAL SOURCE:
         (A) ORGANISM: Homo sapiens (vii) IMMEDIATE SOURCE:
         (B) CLONE: COLLAGEN ALPHA 1 (III)

(xi) SEQUENCE DESCRIPTION: SEQ ID NO:21:

Gln Asn Tyr Ser Pro Gln Tyr Asp Ser Tyr Asp Val Lys Ser Gly Gly
1               5                  10                  15

Val Ala Val Gly Gly Leu Ala Gly Tyr Pro Gly Pro Ala Gly Pro Pro
            20                  25                  30

Gly Pro Pro Gly Pro Pro Gly Thr Ser Gly His Pro Gly Ser Pro Gly
        35                  40                  45

Ser Pro Gly Tyr Gln Gly Pro Pro Gly Glu Pro Gly Gln Ala Gly Pro
    50                  55                  60

Ser Gly Pro Pro Gly Pro Pro Gly Ala Ile Gly Pro Ser Gly Pro Ala
65                  70                  75                  80

Gly Lys Asp Gly Glu Ser Gly Arg Pro Gly Arg Pro Gly Asp Arg Gly
                85                  90                  95

Leu Pro Gly Pro Pro Gly Ile Lys Gly Pro Ala Gly Ile Pro Gly Phe
            100                 105                 110

Pro Gly Met Lys Gly His Arg Gly Phe Asp Gly Arg Asn Gly Glu Lys
        115                 120                 125

Gly Glu Thr Gly Ala Pro Gly Leu Lys Gly Glu Asn Gly Leu Pro Gly
    130                 135                 140

Glu Asn Gly Ala Pro Gly Pro Met Gly Pro Arg Gly Ala Pro Gly Glu
145                 150                 155                 160

Arg Gly Arg Pro Gly Leu Pro Gly Ala Ala Gly Ala Arg Gly Asn Asp
                165                 170                 175

Gly Ala Arg Gly Ser Asp Gly Gln Pro Gly Pro Pro Gly Pro Pro Gly
            180                 185                 190

Thr Ala Gly Phe Pro Gly Ser Pro Gly Ala Lys Gly Glu Val Gly Pro
        195                 200                 205

Ala Gly Ser Pro Gly Ser Asn Gly Ala Pro Gly Gln Arg Gly Glu Pro
    210                 215                 220

Gly Pro Gln Gly His Ala Gly Ala Gln Gly Pro Pro Gly Pro Pro Gly
225                 230                 235                 240

Ile Asn Gly Ser Pro Gly Gly Lys Gly Glu Met Gly Pro Ala Gly Ile
                245                 250                 255

Pro Gly Ala Pro Gly Leu Met Gly Ala Arg Gly Pro Pro Gly Pro Ala
            260                 265                 270

Gly Ala Asn Gly Ala Pro Gly Leu Arg Gly Gly Ala Gly Glu Pro Gly
        275                 280                 285

Lys Asn Gly Ala Lys Gly Glu Pro Gly Pro Arg Gly Glu Arg Gly Glu
    290                 295                 300

Ala Gly Ile Pro Gly Val Pro Gly Ala Lys Gly Glu Asp Gly Lys Asp
305                 310                 315                 320

Gly Ser Pro Gly Asp Pro Gly Ala Asn Gly Leu Pro Gly Ala Ala Gly
                325                 330                 335

Glu Arg Gly Ala Leu Gly Ser Arg Gly Pro Ala Gly Pro Asn Gly Ile
            340                 345                 350

Pro Gly Glu Lys Gly Pro Ala Gly Glu Arg Gly Ala Pro Gly Pro Ala
```

-continued

```
            355                 360                 365
Gly Pro Arg Gly Ala Ala Gly Glu Pro Gly Arg Asp Gly Val Pro Gly
            370                 375                 380
Gly Pro Gly Met Arg Gly Met Pro Gly Ser Pro Gly Gly Pro Gly Ser
385                 390                 395                 400
Asp Gly Lys Pro Gly Pro Gly Ser Gln Gly Glu Ser Gly Arg Pro
                405                 410                 415
Gly Pro Pro Gly Pro Ser Gly Pro Arg Gly Gln Pro Gly Val Met Gly
                420                 425                 430
Phe Pro Gly Pro Lys Gly Asn Asp Gly Ala Pro Gly Lys Asn Gly Glu
            435                 440                 445
Arg Gly Gly Pro Gly Gly Pro Gly Pro Gln Gly Pro Pro Gly Lys Asn
        450                 455                 460
Gly Glu Tyr Gly Pro Gln Gly Pro Pro Gly Pro Thr Gly Pro Gly Gly
465                 470                 475                 480
Asp Lys Gly Asp Thr Gly Pro Arg Gly Pro Gln Gly Leu Gln Gly Leu
                485                 490                 495
Pro Gly Thr Gly Gly Pro Pro Gly Glu Asn Glu Lys Pro Gly Glu Pro
            500                 505                 510
Gly Pro Lys Gly Glu Ala Gly Ala Pro Gly Ala Pro Gly Gly Lys Gly
            515                 520                 525
Asp Ala Gly Ala Pro Gly Glu Arg Gly Pro Pro Gly Leu Ala Gly Ala
530                 535                 540
Pro Gly Leu Arg Gly Gly Ala Gly Pro Pro Gly Pro Glu Gly Gly Lys
545                 550                 555                 560
Gly Ala Ala Gly Pro Pro Gly Pro Pro Gly Ala Ala Gly Thr Pro Gly
                565                 570                 575
Leu Gln Gly Met Pro Gly Glu Arg Gly Gly Leu Gly Ser Pro Gly Pro
                580                 585                 590
Lys Gly Asp Lys Gly Glu Pro Gly Gly Pro Gly Ala Asp Gly Val Pro
            595                 600                 605
Gly Lys Asp Gly Pro Arg Gly Pro Thr Gly Pro Ile Gly Pro Pro Gly
        610                 615                 620
Pro Ala Gly Gln Pro Gly Asp Lys Gly Glu Gly Gly Ala Pro Gly Leu
625                 630                 635                 640
Pro Gly Ile Ala Gly Pro Arg Gly Ser Pro Gly Glu Arg Gly Glu Thr
                645                 650                 655
Gly Pro Pro Gly Pro Ala Gly Phe Pro Gly Ala Pro Gly Gln Asn Gly
                660                 665                 670
Glu Pro Gly Gly Lys Gly Glu Arg Gly Ala Pro Gly Glu Lys Gly Glu
            675                 680                 685
Gly Gly Pro Pro Gly Val Ala Val Pro Pro Gly Gly Ser Gly Pro Ala
            690                 695                 700
Gly Pro Pro Gly Pro Gln Gly Val Lys Gly Glu Arg Gly Ser Pro Gly
705                 710                 715                 720
Gly Pro Gly Ala Ala Gly Phe Pro Gly Ala Arg Gly Leu Pro Gly Pro
                725                 730                 735
Pro Gly Ser Asn Gly Asn Pro Gly Pro Pro Gly Pro Ser Gly Ser Pro
                740                 745                 750
Gly Lys Asp Gly Pro Pro Gly Pro Ala Gly Asn Thr Gly Ala Pro Gly
            755                 760                 765
Ser Pro Gly Val Ser Gly Pro Lys Gly Asp Ala Gly Gln Pro Gly Glu
770                 775                 780
```

```
Lys Gly Ser Pro Gly Ala Gln Gly Pro Pro Gly Ala Pro Gly Pro Leu
785                 790                 795                 800

Gly Ile Ala Gly Ile Thr Gly Ala Arg Gly Leu Ala Gly Pro Pro Gly
                805                 810                 815

Met Pro Gly Pro Arg Gly Ser Pro Gly Pro Gln Gly Val Lys Gly Glu
                820                 825                 830

Ser Gly Lys Pro Gly Ala Asn Gly Leu Ser Gly Glu Arg Gly Pro Pro
            835                 840                 845

Gly Pro Gln Gly Leu Pro Gly Leu Ala Gly Thr Ala Gly Glu Pro Gly
        850                 855                 860

Arg Asp Gly Asn Pro Gly Ser Asp Gly Leu Pro Gly Arg Asp Gly Ser
865                 870                 875                 880

Pro Gly Gly Lys Gly Asp Arg Gly Glu Asn Gly Ser Pro Gly Ala Pro
                885                 890                 895

Gly Ala Pro Gly His Pro Gly Pro Pro Gly Pro Val Gly Pro Ala Gly
                900                 905                 910

Lys Ser Gly Asp Arg Gly Glu Ser Gly Pro Ala Gly Pro Ala Gly Ala
            915                 920                 925

Pro Gly Pro Ala Gly Ser Arg Gly Ala Pro Gly Pro Gln Gly Pro Arg
        930                 935                 940

Gly Asp Lys Gly Glu Thr Gly Glu Arg Gly Ala Ala Gly Ile Lys Gly
945                 950                 955                 960

His Arg Gly Phe Pro Gly Asn Pro Gly Ala Pro Gly Ser Pro Gly Pro
                965                 970                 975

Ala Gly Gln Gln Gly Ala Ile Gly Ser Pro Gly Pro Ala Gly Pro Arg
                980                 985                 990

Gly Pro Val Gly Pro Ser Gly Pro Pro Gly Lys Asp Gly Thr Ser Gly
            995                 1000                1005

His Pro Gly Pro Ile Gly Pro Pro Gly Pro Arg Gly Asn Arg Gly Glu
        1010                1015                1020

Arg Gly Ser Glu Gly Ser Pro Gly His Pro Gly Gln Ser Gly Pro Pro
1025                1030                1035                1040

Gly Pro Pro Gly Ala Pro Gly Pro Cys Cys Gly Gly Val Gly Ala Pro
                1045                1050                1055

Ala Ile Ala Gly Ile Gly Ala Glu Lys Ala Gly Gly Phe Ala Pro Tyr
                1060                1065                1070

Tyr Gly Asp Glu Pro Met
            1075
```